United States Patent
Balthes et al.

(10) Patent No.: US 11,474,061 B2
(45) Date of Patent: Oct. 18, 2022

(54) METHOD AND DEVICE FOR DETERMINATION OF WATER CONTENT

(71) Applicant: Boehringer Ingelheim International GmbH, Ingelheim am Rhein (DE)

(72) Inventors: Eduard Balthes, Ingelheim am Rhein (DE); Kathrin Salzmann, Ingelheim am Rhein (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 1103 days.

(21) Appl. No.: 15/548,458

(22) PCT Filed: Feb. 2, 2016

(86) PCT No.: PCT/EP2016/000162
§ 371 (c)(1),
(2) Date: Aug. 3, 2017

(87) PCT Pub. No.: WO2016/124326
PCT Pub. Date: Aug. 11, 2016

(65) Prior Publication Data
US 2018/0136155 A1   May 17, 2018

(30) Foreign Application Priority Data
Feb. 3, 2015   (EP) .................... 15000304

(51) Int. Cl.
G01R 27/08   (2006.01)
G01N 27/04   (2006.01)
(Continued)

(52) U.S. Cl.
CPC ............ G01N 27/048 (2013.01); A61J 1/035 (2013.01); G01N 27/041 (2013.01); G01N 33/15 (2013.01)

(58) Field of Classification Search
CPC .... G01N 27/041; G01N 27/048; G01N 27/12; G01N 27/121; G01N 27/122; G01N 27/125; G01N 33/15; A61J 1/035
See application file for complete search history.

(56) References Cited

U.S. PATENT DOCUMENTS 4,531,087 A * 7/1985 Larson ................... G01R 27/02
324/696
4,657,133 A   4/1987 Komatsu et al.
(Continued)

FOREIGN PATENT DOCUMENTS

DE   10 2007 034 156 A1   1/2009
EP    1 345 027 A1        9/2003
(Continued)

*Primary Examiner* — Thang X Le
(74) *Attorney, Agent, or Firm* — David S. Safran; Calderon Safran & Cole P.C.

(57) ABSTRACT

A method for determining water content of a preferably solid pharmaceutical preparation/sample, wherein at least two electrodes are brought into direct contact with the pharmaceutical preparation/sample in a measurement chamber such that the electrodes are electrically connected to one another via the pharmaceutical preparation/sample, and wherein a resistance of the pharmaceutical preparation/sample is determined by means of the electrodes and the water content and/or the sample quality of the pharmaceutical preparation/sample is determined with the ohmic resistance.

18 Claims, 5 Drawing Sheets

(51) Int. Cl.
 *G01N 33/15* (2006.01)
 *A61J 1/03* (2006.01)

(56) References Cited

U.S. PATENT DOCUMENTS

| | | | |
|---|---|---|---|
| 5,028,906 A * | 7/1991 | Moriya | G01N 27/121 |
| | | | 338/35 |
| 5,730,024 A * | 3/1998 | Sahlen | G01N 33/383 |
| | | | 73/73 |
| 8,912,891 B2 | 12/2014 | Balthes et al. | |
| 8,915,121 B2 | 12/2014 | Kumar et al. | |
| 10,215,786 B2 | 2/2019 | Kietzmann et al. | |
| 2002/0000814 A1* | 1/2002 | Robinson, Jr. | G01N 33/12 |
| | | | 324/692 |
| 2005/0104596 A1* | 5/2005 | Fleury | G01N 27/02 |
| | | | 324/376 |
| 2006/0164106 A1* | 7/2006 | Jennings | G01N 27/223 |
| | | | 324/664 |
| 2006/0201602 A1* | 9/2006 | Nair | B32B 33/00 |
| | | | 156/64 |
| 2010/0156439 A1 | 6/2010 | Schroeder et al. | |
| 2011/0187375 A1* | 8/2011 | Capaccioli | G01N 27/041 |
| | | | 324/376 |
| 2011/0290649 A1* | 12/2011 | Hamada | B03C 5/005 |
| | | | 204/547 |
| 2013/0313111 A1* | 11/2013 | Nishida | G01N 27/02 |
| | | | 204/415 |
| 2015/0021326 A1* | 1/2015 | Giraud | B65D 83/0409 |
| | | | 220/254.1 |

FOREIGN PATENT DOCUMENTS

| | | |
|---|---|---|
| JP | S372099 | 2/1962 |
| JP | H06-1359 A | 1/1994 |
| JP | H10-225501 A | 8/1998 |
| JP | 2004340803 A | 12/2004 |
| JP | 2007285913 A | 11/2007 |
| JP | 2008164441 A | 7/2008 |
| JP | 2011149771 A | 8/2011 |

* cited by examiner

METHOD AND DEVICE FOR DETERMINATION OF WATER CONTENT

BACKGROUND OF THE INVENTION

Field of the Invention

This invention relates to a method for determining the water content of a sample, in particular of a pharmaceutical preparation and/or of a packaging material, a use, a measurement chamber, a package and a method. This invention relates in particular to the field of pharmaceuticals, in particular the choice and construction of packages for pharmaceutical preparations.

Description of Related Art

It has been shown that the water content of a pharmaceutical preparation and/or of a packaging material has a distinct effect on the stability of the pharmaceutical preparation. The invention furthermore relates to the exact determination of the water content of a pharmaceutical preparation/sample and the simulation of stabilities of the pharmaceutical preparation/sample packed in the respective package in order to determine an especially suitable or economical package. For this purpose, it is especially desirable to determine as quickly and exactly as possible the water content of a plurality of samples of a pharmaceutical preparation and/or of a packaging material.

Methods in which conclusions about the original water content are drawn by a drying process are known and conventional in the field of pharmaceuticals.

These methods include difference weighings in which a wet sample, in particular in the form of the pharmaceutical preparation and/or the packaging material, are weighed, afterwards dried as the temperature rises, and thereupon weighed again. Alternatively or in addition, desiccants for drying of the samples, in particular in the form of pharmaceutical preparations and/or packaging materials, can also be used. Then, the original water content of the sample, in particular in the form of the pharmaceutical preparation and/or the packaging material, can be concluded from the weight difference.

In Karl Fischer titration, a sample is dissolved in a suitable solvent and the water which has gone into solution is detected with a subsequent titration.

In the calcium carbide method, the pharmaceutical preparation together with calcium carbide is placed in a pressure-tight vessel in which the water from the sample reacts with the calcium carbide, forming acetylene, as a result of which an overpressure forms which can be measured with a pressure gauge and which corresponds to the amount of water contained in the sample.

It is common to the aforementioned methods that they are accurate enough for many applications, but are very laborious and time-consuming.

Additionally, methods are known from the field of determining residual moisture contents in wood or structures in which electrical conductivity is determined, and on this basis, water content is estimated. The tolerances of several percent which are conventional in doing so are acceptable for a decision whether wood is dry enough for burning (whether a) or—masonry has moisture damage, but not for this domain of pharmaceuticals. Therefore, these methods are not used for pharmaceuticals.

SUMMARY OF THE INVENTION

One object of this invention is an accurate, quick, simple, nondestructive, broadly usable method for measuring moisture content to ensure product stability by use in quality control (for example, goods receipt, processing and storage of product components, intermediate products, bulk goods, components of packing means, packaging systems and the packaged product) as well as at-line, on-line or even in-line of production or packing processes.

The object of this invention is to devise a method for determining the water content of a sample, in particular a pharmaceutical preparation and/or a packaging material, a use as well as a measurement chamber and a package, as a result of which a determination of the water content of the sample, in particular of the pharmaceutical preparation and/or the packaging material, can be carried out more quickly and/or exactly, in particular so that the determination of moisture content of larger measurement series with a plurality of samples, in particular pharmaceutical preparation samples and/or packaging material samples, can be implemented manageably and/or faster.

This object is achieved by a method, a measurement chamber, a package in accordance with the invention as described herein.

The invention is explained below in general relative to "samples". But it is preferred that the sample/samples are one/several pharmaceutical preparations. In this connection, some aspects of this invention which are described below have been found to be especially advantageous. Therefore, the term "sample" within the scope of this invention can if necessary be replaced by the term "pharmaceutical preparation" or can be combined into the term "pharmaceutical preparation sample".

Alternatively or in addition, the sample is formed by a packaging material. Consequently, the term "sample" used below within the scope of this invention can be replaced by the term "packaging material" or added to the term "packaging material sample".

Altogether, the term "sample" within the scope of this invention can also always be replaced by the combination "pharmaceutical preparation and/or packaging material".

Hereafter, primarily the term "pharmaceutical preparation/sample" is essentially used, which means the "pharmaceutical preparation and/or sample" and consequently by subsequent deletion of an alternative being able to be limited to "sample" or "pharmaceutical preparation". Furthermore, the use of "sample/pharmaceutical preparation" takes place for better understanding. Here, the terms "sample" or "pharmaceutical preparation" can also be replaced or supplemented as described above.

Furthermore, the invention is explained using specific exemplary embodiments relative to one or more pharmaceutical preparations. But, preferably this invention is not limited to "pharmaceutical preparations" in this context either. Therefore, the term "pharmaceutical preparations" can preferably be replaced by the term "sample", the term "packaging material", or the combination of "pharmaceutical preparation and/or packaging material". This applies in any case to the extent the respective context does not logically conflict with a replacement.

This invention relates on a priority basis to the measurement of the moisture content of samples, preferably in the form of solid pharmaceutical formulations, their packages, components of packing means, in particular desiccants and films, as well as devices for pharmaceutical applications using their electrical conductivity.

The term "sample" or "pharmaceutical preparation" is defined preferably alternatively or additionally as the following: pharmaceutical products (for example, tablets, powders, granulates, solid formulations, capsule, adjuvants), active ingredients, raw materials, premixtures, intermediate products of pharmaceutical preparations, capsules as well as packing means (films, sealing waxes, granular desiccants, desiccant-containing moldings, polymer-based bottles, polymer-based devices, especially for inhalants, for pediatric applications, for veterinary applications, devices developed for diagnostic purposes), packages, devices with potential use in development and/or individual parts of these components.

In particular, the determination of the electrical conductivity can be used as a quick method for preliminary studies with respect to the sample quality of active pharmaceutical ingredients and/or adjuvants. To do this, preferably the conductivity—preferably via its relationship to moisture content or water content—is assigned to a sample quality. In this way, conclusions about sample quality can be drawn from the determined conductivity, directly or indirectly. Also, in this way, a quality indicator can be generated, determined and/or output correspondingly to the sample quality. The quality indicator can be or consider solely the moisture content or water content of the sample or additionally also can be or consider one or more other quality- and/or stability-determining parameters.

A first aspect of this invention relates to a method for determining the water content of a sample, in particular a sample in the form of a pharmaceutical preparation and/or packaging material, wherein a measurement chamber with at least two electrodes is provided and the pharmaceutical preparation/sample is brought into direct contact with these electrodes. This takes place such that the electrodes are connected to one another by the pharmaceutical preparation/sample and/or separated from one another, the electrodes therefore being electrically in contact with one another preferably solely via the pharmaceutical preparation/sample and/or not being electrically directly in contact. The electrodes are then preferably in contact with one another via the pharmaceutical preparation/sample. Furthermore one, in particular electrical and/or ohmic resistance of the pharmaceutical preparation/sample is determined by means of the electrodes and with the resistance the water content of the pharmaceutical preparation/sample is determined.

It has been surprisingly shown that, against the existing biases, a determination of the water content of a pharmaceutical preparation/sample by determining the resistance of the latter is not only very quick, but can also be very exact. The use of a measurement chamber in which preferably the electrode and the pharmaceutical preparation/sample are located contributes significantly thereto. In the measurement chamber, specifically, a defined environment including a specific atmosphere surrounding the pharmaceutical preparation/sample and reproducible transition between the electrodes and the pharmaceutical preparation/sample can be achieved; this leads in a synergetic manner to a more precise determination of the water content compared to known resistance-based methods than could be expected.

The invention enables exact and/or quick and/or easily performed and/or nondestructive (without destroying the sample or the shape, presentation, surface or peripheral line of the sample) and/or broadly usable and/or versatile method for measurements of moisture content, preferably using the electrical conductivity.

Furthermore, it has been surprisingly shown that, with this invention, a more exact determination of the moisture content and/or water content of the pharmaceutical preparation/sample is enabled. The increased accuracy makes it possible to reduce safety margins or safety impacts. For example, it is possible by exact determination of the moisture content or water content of the pharmaceutical preparation/sample to keep the amount of desiccant to be provided within the package low and consequently enable resource-conserving packaging.

It is preferred that, to determine the water content, an assignment means is used, in particular an assignment table or assignment function. Preferably, water content of the pharmaceutical preparation/sample is determined with a reference measurement method, a resistance determined at the same water content of the pharmaceutical preparation/sample is assigned by the assignment means. Reference methods are, for example, the methods named in the introduction of the specification in which precise conclusions about the original water content can be drawn by a drying process.

It is provided in particular that an assignment table or assignment function or some other assignment means is specific to a quite defined pharmaceutical preparation/sample, preferably with different water contents, or is intended for this purpose.

For different pharmaceutical preparation/samples, in particular therefore pharmaceutical preparations/samples with different formulations or compositions, several and/or different corresponding assignment means can be defined, provided and/or used.

It has been surprisingly shown that, even for similar formulations of pharmaceutical preparations/samples, the resistances which are dependent on the water content can diverge significantly from one another and consequently individual assignment means are beneficial to the accuracy of determining the water content.

With the assignment means, preferably a water content corresponding to the resistance is determined, in particular by a value corresponding to the respectively determined resistance being taken from the assignment table, calculated with the assignment function or determined with the other assignment means. The water content or a stability of the pharmaceutical preparation/sample determined therefrom is/are output preferably as the result. This enables quick and accurate determination of the water content or an especially advantageous package since using exact water contents optionally the amount of required desiccant in a package or the amount of packaging material can be reduced or changed or the complexity of the package can be reduced.

Especially preferably, the assignment means is alternatively or additionally specific to certain electrodes or vice versa. Therefore, it can be provided that, for the same pharmaceutical preparation/sample, different assignment means for the use of different electrodes are provided or used, in particular (automatically) chosen. This can avoid differences in the contact surfaces between the electrodes and the pharmaceutical preparation/sample leading to deviations.

The electrodes are preferably always connected to the pharmaceutical preparation/sample such that direct contact of the electrodes with one another is prevented and/or the electrodes with the pharmaceutical preparation/sample form a series circuit. A current applied to an electrode consequently flows through the pharmaceutical preparation/sample into the other electrode(s). There can be more than two electrodes. In this way different resistances of the same pharmaceutical preparation/sample can be determined in different directions by the pharmaceutical preparation/sample. In this way, inhomogeneous water distributions can be advantageously identified or taken into account. However, versions with two electrodes are always preferably described below.

Preferably, electrodes corresponding to a certain formulation and/or presentation, in particular the silhouette or shape of the surface of the pharmaceutical preparation/sample are mounted in the measurement chamber. Preferably the electrodes have contact surfaces for connection to the pharmaceutical preparation/sample which are made at least essentially as a negative picture of a surface segment of the pharmaceutical preparation/sample. In this way it is ensured for the respectively current presentation of the pharmaceutical preparation/sample that a defined and sufficiently large contact surface between the pharmaceutical preparation/sample and the electrodes can be produced; this benefits the reproducibility and exactness of the determination of the water content of the pharmaceutical preparation/sample.

According to one preferred embodiment, it is provided that the electrodes are replaced when the presentation of the pharmaceutical preparation/sample is changed for a further measurement. The electrodes can therefore preferably be interchangeable, in particular automatically by a changing system, a revolver system or the like.

The electrodes are preferably connected to a measurement apparatus for measuring the resistance of the pharmaceutical preparation/sample. The measurement apparatus can be in particular an electrometer. The measurement principle of an electrometer has been shown to be especially advantageous for exact and reproducible as well as quick determination of the water content of pharmaceutical preparations/samples. In doing so it is provided that a defined voltage change is applied to the pharmaceutical preparation/sample and a differential current through the pharmaceutical preparation/sample which arises by the voltage or voltage change is measured. But basically, other methods can also be used, for example, those in which a (differential) current is applied and the resulting (differential) voltage is measured.

To determine the resistance of the pharmaceutical preparation/sample preferably a current flowing through the pharmaceutical preparation/sample and a voltage dropping over the pharmaceutical preparation/sample are determined. The respective resistance can be calculated by division of the respective voltage by the respective current.

Preferably, one such or corresponding calculation is not based on an absolute current and voltage value. Instead it is especially preferred that the determination of the resistance is based on differential voltages and differential currents. In doing so, the voltage on the electrodes or over the pharmaceutical preparation/sample can be changed. This voltage change corresponds to a differential voltage or voltage difference. Based on the voltage change, a change of the current flowing through the pharmaceutical preparation/sample, therefore a differential current or a current differential, takes place, in particular according to Ohm's law. The quotient of the differential voltage to the differential current, namely the differential voltage divided by the corresponding differential current, likewise complies with the resistance of the pharmaceutical preparation/sample.

The advantage of this method over a classic determination of the resistance with absolute current and voltage quantities lies in that this determination principle is independent of disturbances which lead to a constant error or offset. For example, a DC voltage coupled into the measurement apparatus or a direct component produced by contact transitions or the like is prevented from influencing or adulterating the measurement. This has been found to be especially advantageous for exact determination of the resistance and furthermore of the water content.

For measurement purposes, preferably the voltage on or over the pharmaceutical preparation/sample is changed and the change of the current flowing through the pharmaceutical preparation/sample which has resulted from this voltage change is determined, in particular measured. Alternatively or in addition, the current flowing through the pharmaceutical preparation/sample can be changed and a voltage change resulting therefrom is determined or measured. But, it is fundamentally also possible to change the current flowing through the pharmaceutical preparation/sample and the voltage on the pharmaceutical preparation/sample at the same time or in alternation, preferably the relations between the current and voltage or the current change and the voltage change always being determined or influenced by the resistance of the pharmaceutical preparation/sample and consequently the resistance being able to be determined, in particular calculated by the respective current-voltage relations.

Determination of the resistance is especially preferable by the polarity, the direction and the sign of a voltage applied for this purpose or a current applied for this purpose being reversed several times. This takes place however preferably only for detection and elimination of disturbances and not for influencing the results by capacitive and/or inductive behavior. Against this background, preferably a polarization change is carried out solely at an interval of one or more seconds and/or in which for the measurement, a transient recovery time of one or more seconds is waited.

In one advantageous development, the pharmaceutical preparation/sample within the measurement chamber is brought into direct contact with the pharmaceutical preparation/sample with a defined or definable pressure of the electrodes on the pharmaceutical preparation/sample. For this purpose, a clamp means can be provided which can press the electrodes with a given force against the pharmaceutical preparation/sample. Alternatively or in addition there can be a pressure sensor with which the contact pressure of the contacts on the pharmaceutical preparation/sample can be monitored, controlled and/or adjusted. This advantageously prevents the properties of the pharmaceutical preparation/sample and of the electrical contacts of the electrodes with the pharmaceutical preparation/sample, in particular after a sample change and/or a replacement of the pharmaceutical preparation/sample, from varying and possibly leading to uncertainties and tolerances.

The water content of an atmosphere surrounding the pharmaceutical preparation/sample within the measurement chamber is preferably set or specified. This prevents water absorption into the pharmaceutical preparation/sample or water release from the pharmaceutical preparation/sample before or during the measurement from leading to inaccuracies. This applies in particular to calibration measurements.

It is provided in particular that in the measurement chamber there is a conditioning agent, in particular a desiccant, moisturizer and/or a saturated salt solution or the like.

Preferably, a relative humidity of the atmosphere within the measurement chamber, especially, a (relative) air humidity in the measurement chamber, is specified and/or set, in particular with the conditioning agent. In one preferred version this can take place such that absorption or release of water by the pharmaceutical preparation/sample is reduced or avoided. In this way, any influence on the resistance by the measurement environment can be advantageously avoided.

Furthermore, it is preferred that the same composition of the atmosphere is used in the chamber as the one which is used in intended packaging of the pharmaceutical preparation/sample. In this way, improved accuracy of the determination of the water content can be achieved by precluding any influence of the gaseous phase or atmosphere surrounding the pharmaceutical preparation/sample on the measurement process, for example, by physical and/or chemical change of the pharmaceutical preparation/sample. The measurement chamber can be filled or fillable with a gas, in particular a protective gas, as the atmosphere for this purpose.

According to one aspect of this invention which can also be independently implemented, it is especially preferred that for the determination of the water content of the pharmaceutical preparation/sample after completion of an exposed storage study in which the pharmaceutical preparation/sample has been exposed to defined ambient conditions over a certain time interval, these ambient conditions within the chamber are retained, set or specified in order to not adulterate the effect of the ambient conditions of the exposed storage study during the measurement. For example, in an exposed storage study a quite certain temperature and a quite certain (relative) air humidity of the vicinity are set and the pharmaceutical preparation/sample is exposed in the open to these ambient conditions over a specified time interval. It is then preferred for the measurement that in the measurement chamber the same ambient conditions, in particular therefore the same temperature and/or (relative) air humidity, is/are set. This aspect is also advantageous when the determination of the water content takes place in some way other than by resistance measurement, even if the resistance measurement is especially preferred and is accompanied by additional synergisms and advantages. The use of this aspect is especially advantageous in conjunction with calibration measurements or calibration steps or calibration in general. In doing so a relationship between the resistance and the water content can be determined.

With the results, therefore with the water content or a value corresponding thereto which has been determined with the proposed method, the stability of the pharmaceutical preparation/sample can be calculated and/or forecast in the following, especially in storage in a certain form of packaging. In doing so, it is preferred that, in addition to the water content of the pharmaceutical preparation/sample, the water content of the packaging material and of the atmosphere enclosed in the packaging process is determined and thereupon with a sorption model or the like the moisture absorption through the package and the moisture exchange between the different materials, especially therefore the package, the atmosphere and the pharmaceutical preparation/sample is simulated within the package. Conclusions about the water absorption by the pharmaceutical preparation/sample and/or the stability or degeneration of the pharmaceutical preparation/sample can be drawn.

In another aspect of this invention which can also be independently implemented, the resistance of a pharmaceutical preparation/sample is determined or calculated to determine the water content of the pharmaceutical preparation/sample and/or to predict the stability of the pharmaceutical preparation/sample, preferably in a certain package form.

Another aspect of this invention which can also be independently implemented relates to a measurement chamber for determining a resistance of a pharmaceutical preparation/sample. The measurement chamber has at least two electrodes and is made to accommodate the pharmaceutical preparation/sample and bring it into direct contact with the electrodes such that the electrodes are electrically connected to one another by the pharmaceutical preparation/sample and/or are spatially separated from one another. It is furthermore provided that the measurement chamber can be sealed airtight so that the measurement chamber encloses an atmosphere which surrounds the pharmaceutical preparation/sample, the measurement chamber being set up to adjust the water content of the atmosphere surrounding the pharmaceutical preparation/sample.

To determine the water content of an uncompacted pharmaceutical preparation/sample, therefore a powder, granulate, or the like, at least one of the electrodes can have a receiver or cavity which can accommodate the pharmaceutical preparation/sample, the receiver being made to enable a contact of the pharmaceutical preparation/sample with the electrodes without the electrodes being directly electrically connected to one another. In particular, one of the electrodes forms a bottom plate of the receiver and the second electrode can enter the receiver as a punch and compress the pharmaceutical preparation/sample in the receiver. Here, however, other approaches are also possible.

Preferably, the measurement chamber has a conditioning means for influencing or setting the (relative) humidity of the atmosphere. Preferably, within the measurement chamber next to the electrodes, there are suitable means, in particular a container, a fastener or the like, by means of which the conditioning means can be positioned within the chamber such that the water content, the moisture or relative humidity of the atmosphere can be adjusted or influenced by the conditioning means, the conditioning means however not acquiring any direct contact with the electrodes or the pharmaceutical preparation/sample in order to preclude adulteration of the measurement.

The electrodes are or can preferably be located at least in the region of the contact surfaces for the pharmaceutical preparation/sample within the measurement chamber. The chamber can be bordered by an especially airtight chamber wall. The chamber can preferably be opened, in particular divided such that the pharmaceutical preparation/sample can be placed in the chamber and connected to the electrodes.

The electrodes which are provided in the measurement chamber are preferably made corresponding to a shape and/or composition of the pharmaceutical preparation/sample. In particular, it is provided that the electrodes have contact surfaces which are formed complementary to the external shape or to segments of the external shape of the respective pharmaceutical preparation/sample. This results in that a reproducible and sufficient large contact surface between the electrodes and the pharmaceutical preparation/sample can be achieved.

The electrodes are preferably interchangeably held in the measurement chamber. This advantageously results in that electrodes corresponding to the shape and/or composition of the pharmaceutical preparation/sample can be chosen and/or can be mounted in the measurement chamber.

Furthermore, it is preferred that the electrodes have a clamping means and/or a force measuring apparatus, as a result of which the electrodes can be pressed against the pharmaceutical preparation/sample with a definable and/or reproducible force. This is beneficial as well as advantageous both for the reproducibility of determining the water content of the pharmaceutical preparation/sample in that the adverse mechanical effect on the pharmaceutical preparation/sample by overly great forces acting on the latter can be avoided.

The electrodes are held in the measurement chamber preferably to be able to move relative to one another so that the electrodes can be pressed against the pharmaceutical preparation/sample located between the electrodes. In particular therefore, at least one of the electrodes can travel and/or slide, can be moveable or can move in some other way. In this way, the electrodes can be moved apart from one another for insertion of the pharmaceutical preparation/sample and after placing the pharmaceutical preparation/sample between the electrodes they can be brought into direct contact with the pharmaceutical preparation/sample. To do this, the electrodes are preferably pressed against the pharmaceutical preparation/sample with a pressure force.

The measurement chamber preferably has a measurement apparatus which is made for measuring the resistance of the pharmaceutical preparation/sample. The measurement apparatus can be or can have an electrometer and/or can be made for determination of the resistance based on a measurement of differential voltages and differential currents.

The electrodes are preferably electrically connected to the measurement apparatus. To do this the electrodes can be connected to electrically conductive cables which lead in particular out of the measurement chamber and electrically connect the electrodes to the measurement apparatus. The cables are preferably shielded and/or antistatic to prevent adulterations of the respective measurement. The measurement apparatus is preferably located outside the chamber and/or the atmosphere.

The measurement chamber preferably has a moisture sensor for determination of the (relative) humidity of the atmosphere. In this way, it can be monitored and/or controlled whether the (relative) humidity of the atmosphere is correctly set by the conditioning means or in some other way. Alternatively or in addition, the (relative) humidity of the atmosphere can be controlled or adjusted by the moisture sensor. For example, depending on a measured value of the moisture sensor the amount or the action of the conditioning means can be influenced, in particular by changing the amount of conditioning means, by (partial) covering and/or by replacing and/or moving the atmosphere.

It is preferred that the moisture determination apparatus and/or the assignment means consider or eliminate unwanted, so-called parasitic effects of the measurement arrangement including the instrument leads and electrodes. Calibration can take place for this purpose. Preferably, for calibration, a short circuit is established between the electrodes, as a result of which resistance fractions of the measurement arrangement are determined or measured which are subsequently considered in the determination of the resistance of the pharmaceutical preparation/sample, in particular are subtracted.

Furthermore, it is preferred that the measurement chamber have a moisture determination apparatus for determination and preferably output of the water content of the pharmaceutical preparation/sample which corresponds to the determined resistance. The moisture determination apparatus can have the assignment means for this purpose or can access the assignment means and after measuring the resistance determine a water content which corresponds to the ascertained resistance, for example, by reading out a corresponding value from an assignment table or by insertion into an assignment function.

Furthermore, the measurement chamber preferably has a stability determination apparatus which is made to calculate with the water content a stability of the pharmaceutical preparation/sample in a certain package and preferably output it. It is therefore in particular provided that one or more measurements of the measurement apparatus are automatically evaluated with one or more samples of the pharmaceutical preparation/sample and are used in combination with properties of packages to forecast the stability of the pharmaceutical preparation/sample packed in one or more certain packages and preferably by comparison of the forecasts to choose an advantageous suitable package or make available a corresponding selection of suitable packages.

A water content within the scope of this invention is preferably the fraction of water which can be removed from a substance and/or pharmaceutical preparation/sample by drying. In particular the term "water content" is understood such that it corresponds to the water content which is determined with the known reference methods such as Dynamic Vapor Sorption Weighing (DVS Weighing), Karl Fischer titration or the gravimetric drying oven method.

It is possible that in the determination of the electrical resistance both free and also bound water are considered, since the two contribute to conductivity: free water for example, by direct ion transport and release of further ions; bound water by thermally activated direct ion transport and by release of ions, for example, via a change of the crystal structure or a change of the background crystal field and thus of the Fermi energy.

Electrodes within the scope of this invention are preferably elements with electrically conducting surfaces which are made to produce and/or to make direct and/or galvanic contact with a substance, in particular the pharmaceutical preparation/sample. The electrodes can be made of metal or can contain metal, preferably a precious metal like gold or platinum. However, fundamentally, other electrically conductive materials can be used.

Preferably, the term "resistance" within the scope of this invention always means electrical and/or ohmic resistance of the pharmaceutical preparation/sample, in particular between the electrodes, except for something else arising from the context or the explanation. Within the scope of this invention, a resistance is preferably a so-called DC resistance and/or real part of an impedance. Alternatively or in addition, however, reactive behavior can also be considered, for example, capacitive behavior of the pharmaceutical preparation/sample.

Within the scope of this invention, a pharmaceutical preparation/sample is preferably a substance which has one or more active substances and/or ingredients and/or one or more adjuvants.

Active ingredients and/or active substances are preferably physiologically active substances which are suited to acting on a body of a living being or its functions in a beneficial, healing or some other manner.

Adjuvants are in particular pharmaceutical carriers or ingredient and/or active substance carriers. Adjuvants are preferably pharmacologically and/or toxicologically inert. Adjuvants can be made to carry the active substance and/or ingredient, to influence or enhance the action of the ingredient and/or active substance, to impart to the pharmaceutical preparation/sample its shape, to improve production steps, to control the duration and speed of active substance and/or ingredient release and/or to stabilize the pharmaceutical preparation/sample mechanically or chemically in order to achieve sufficient stability.

The pharmaceutical preparation/sample within the scope of this invention is preferably a solid, in particular at room temperature or 300 K. This solid is preferably present in compact form, in particular capsule form or tablet form, but can also be present in granular form, as a granulate, powder, in the form of spherules or in some other forms. The pharmaceutical preparation/sample can be in particular also a salve, a gel, a cream, a paste, but also a liquid or a gas, although a solid pharmaceutical preparation/sample is preferred.

The term "atmosphere" within the scope of this invention should preferably be understood such that it is a gaseous substance, which in particular is gaseous at normal pressure or ambient pressure, which within the measurement chamber surrounds the pharmaceutical preparation/sample and/or the electrode(s). In particular, it is air, nitrogen and/or protective gas. The atmosphere can have gaseous water, as a result of which depending on the saturation of the atmosphere with water a (relative) humidity of the atmosphere arises.

Preferably, in this invention, the term "current", preferably also combined terms such a "differential current" or "current differential", always means the current which is flowing through the pharmaceutical preparation/sample, except for when the opposite is explicitly mentioned or arises from the context.

When using the term "voltage", preferably also combined terms such a "differential voltage" or "voltage differential" in this invention a voltage which is present or dropping over the pharmaceutical preparation/sample is preferably always meant, if nothing contrary arises from the context or is explained.

Another aspect of this invention which can be independently implemented relates to a package, preferably for granular desiccants, the package preferably being permeable to water vapor at least in segments and having a moisture-sensitive resistance apparatus in which an electrical resistance varies with the change of moisture or with a water content of the resistance apparatus, and electrical contact with the resistance apparatus being possible on different segments, preferably outside the package, so that the contacts and/or segments are electrically connected among one another by the resistance apparatus such that the electrical resistance of the resistance apparatus can be measured. The package preferably has desiccants.

It has been ascertained that corresponding packages can be used by measuring the resistance to be able to draw conclusions easily, quickly and economically about the state of the desiccant or some other substance packed or to be packed with the package.

Preferably, the resistance apparatus is film-like and/or strip-like. Furthermore, it is preferable that the package is formed wholly or in part by the resistance apparatus.

It is preferred that the resistance apparatus is formed by an accompanying strip, preferably the accompanying strip being along the package and/or attached to it.

The resistance apparatus preferably has or is formed from oriented polyamide and/or some other material which has strong moisture dependency of its electrical resistance, preferably such that the electrical resistance measured between a dry and an (atmospherically) humid state of the resistance apparatus according to IEC 60093 differs by more than a factor of 10 or 100, in particular differs more than a factor of 500.

Preferably, the resistance apparatus is arranged and the package is made such that the contents to be packaged in the package is connected or in contact with the resistance apparatus and/or can exchange water or water vapor with the resistance is provided apparatus.

Another aspect of this invention which can also be implemented independently relates to a method for producing a package which is permeable to water vapor at least in parts, which resistance apparatus has a moisture-dependent electrical resistance on and/or in the package.

In particular, the following aspects which can also be implemented independently of one another or in combination are furthermore advantageous.

The moisture content of the packing means, packages and devices is preferably determined using the electrical conductivity.

The measurement and/or the determination of the moisture content of pharmaceutical products, in particular of solid forms, to a particular degree of tablet cores, film tablets, granulates, powders and capsules takes place preferably using the electrical conductivity.

The accuracy of measurement and/or the determination is improved preferably by ensuring the conditioning of the sample in a sealed chamber.

The accuracy of measurement and/or the determination or calibration is achieved preferably by outfitting the chamber with a preconditioning desiccant.

The accuracy of measurement and/or the determination or calibration is improved by using a combination of saturated salt solution and desiccant, for example, silica gel.

The accuracy of measurement and/or the determination or calibration can be improved by suitable electrodes or contact materials, in particular electrodes or contact materials being interchangeable, adapted and/or adaptable in the form of the sample and conductive at the same time.

The accuracy of measurement and/or the determination or calibration can be improved by using pressure and/or compression punches (in particular, identical in shape to the tableting tool) as the electrode.

The measurement accuracy can be improved by combination between DVS and for example, CRDS and/or trace moisture.

Preferably, the moisture content of coatings is measured or the measurement is expanded thereto.

Preferably a moisture content measurement is taken by surface measurements, for example, on film tablets and coatings.

Preferably simplified "platform solutions" are prepared for products with the same coating.

The accuracy of measurement and/or determination and/or the calibration is preferably improved by use of coatings with especially high moisture dependency of the resistance as "applied sensors". The coating closely fits the pharmaceutical preparation, as a result of which a resistance measurement of the coating can be used to draw conclusions about the water content of the pharmaceutical preparation.

The proposed method and/or the resistance measurement is preferably used to determine a sample stability, in particular a correlation between resistance and brittleness, in particular of a gelatin capsule or the like, being determined.

The proposed method and/or the resistance measurement is preferably used to determine a correlation between resistance and hardness of a tablet and/or capsule or other pharmaceutical preparation.

The proposed method and/or the resistance measurement is preferably used with the aid of an auxiliary strip, for example, of OPA, on loose desiccants.

The proposed method or the resistance measurement is preferably applied to loose formulations, for example, powder, granulates, as well as compressed formulations, for example, compactates, tablets, minitablets, for example, in stick packs, and to active substance and/or ingredients and adjuvants.

The accuracy is improved by compacting the loose samples by pressing.

Sample dies are preferably used as electrical contacts.

A pressure dependency of the electrical resistance as an error source is preferably at least essentially eliminated by working at a constant pressure on the sample, in particular in a so-called "pressure plateau".

The proposed method is preferably used for moisture content measurements on adjuvants, active substances and/or ingredients and raw materials.

The proposed method is preferably used for monitoring of hardness, brittleness and/or stickiness on capsules.

The moisture content of packing means is measured preferably indirectly, for example, in packaging films, preferably using a "copy measurement" on a supported material, for example, oPA.

The proposed method is used preferably for measuring unrelaxed samples (for example, in machine standstills).

The accuracy of measurement and/or determination or calibration is improved preferably by conditioning of the tablets in the measurement chamber and by variable air volumes for calibration and measurement.

The accuracy of measurement and/or the determination or calibration is preferably improved by checking the relative humidity by injection/insertion probes.

The accuracy of measurement and/or the determination or calibration is preferably improved by minimizing the leakage currents by special handling (for example, cleaning, gloves, short cable).

Time is saved in the calibration measurement preferably by using a multi-sample DVS apparatus for parallel conditioning of samples.

To improve the accuracy of measurement and/or determination and/or calibration the contact area between the sample and electrodes is enlarged preferably by compressing the samples in the measurement chamber.

Preferably, accuracy is achieved by measurement in the pressure plateau region (optimum compression of the powder) with a powder measurement chamber.

Different aspects of this invention can be combined with one another, in particular the aspects described in conjunction with the proposed method and/or aspects described in conjunction with the proposed measurement chamber individually or together can form part of the proposed use.

Other advantages, aspects, features and properties of this invention will become apparent from the following description of preferred embodiments in conjunction with the accompanying drawings.

DETAILED DESCRIPTION OF THE INVENTION

The same reference numbers are used in the figures for identical or similar parts, wherein the same or similar properties and advantages can be achieved even if a repeated description is omitted.

In the following, the invention is explained in detail using specific exemplary embodiments relating to one or more pharmaceutical preparations. But preferably, this invention is also not limited to "pharmaceutical preparations" in this connection. Therefore, the term "pharmaceutical preparations" can preferably be replaced by the term "sample", the term "packaging material" or the combination "pharmaceutical preparation and/or packaging material". In any case, this applies to the extent the respective context does not logically conflict with the replacement. Therefore, in the following, the term "pharmaceutical preparation/sample" is used. In addition reference is made to the definitions and explanations from the Background part of this application.

Figure 1:
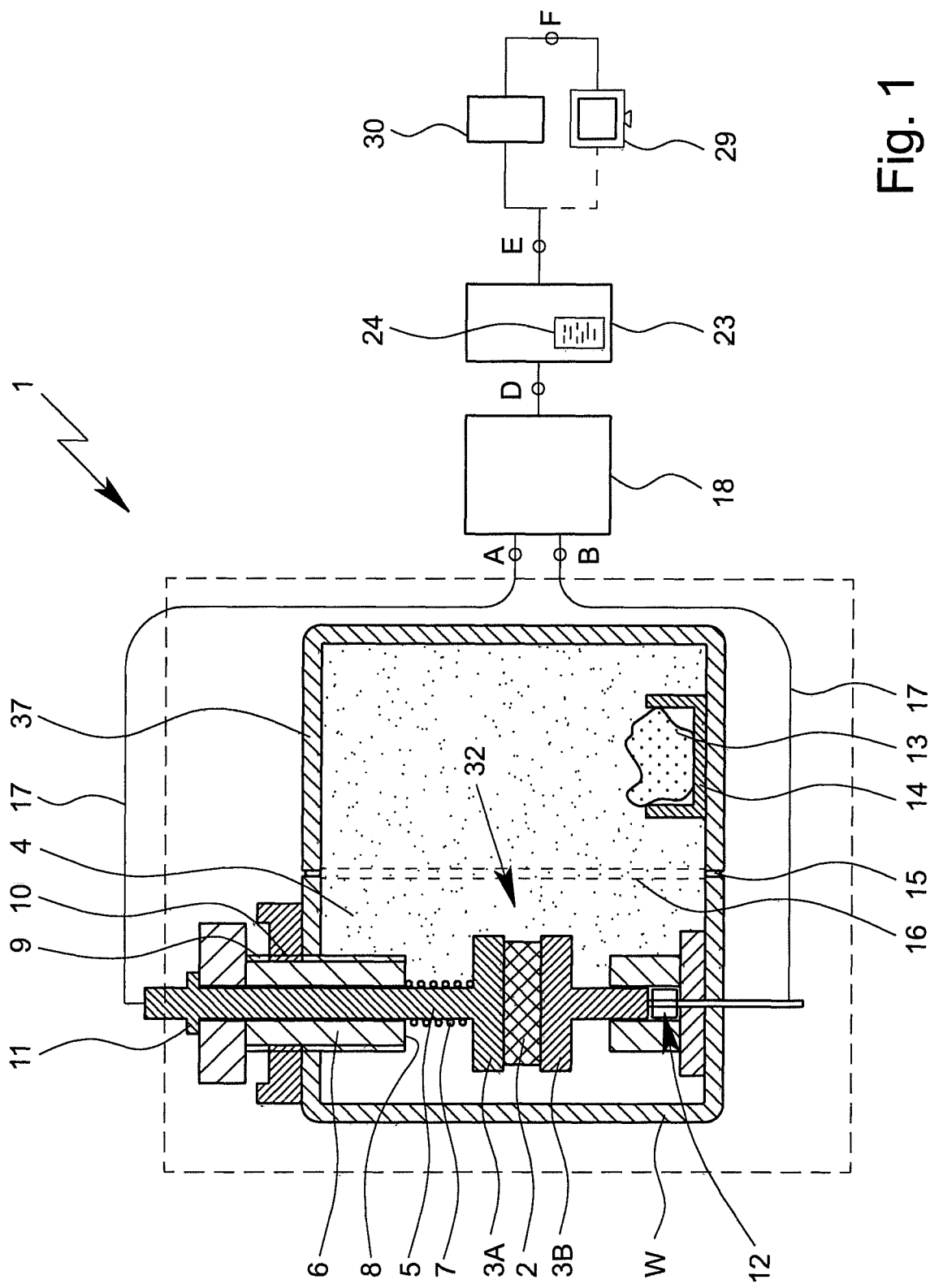
FIG. 1 schematically shows a proposed measurement chamber.

FIG. 1 shows a measurement chamber 1 for determination of a resistance of a pharmaceutical preparation/sample 2. The measurement chamber 1 for this purpose has preferably at least two electrodes 3A, 3B. Furthermore the measurement chamber 1 is made to accommodate the pharmaceutical preparation/sample 2 and bring it into direct contact with the electrodes 3A, 3B such that the electrodes 3A, 3B are galvanically separated from one another by the pharmaceutical preparation/sample 2.

In the exemplary embodiment according to FIG. 1, there is an upper, movable electrode 3A and a lower, preferably stationary electrode 3B. In the following, however, they are always further called electrodes 3 in general to the extent the explanation does not relate to their specific role as an upper or lower electrode.

In the exemplary embodiment according to FIG. 1, at least one electrode 3A, which is preferable the upper one in the position of use can be moveable and/or slidable and/or displaceable. In particular, it is provided that the electrode 3A has a shaft-like or pin-like guide part 5. The guide part 5 is preferably guided in a preferably sleeve-like guide 6. But other approaches are also possible.

The electrode 3A is preferably braced against the pharmaceutical preparation/sample 2 with a clamping means 7. In the illustrated example, the clamping means 7 has a helical spring or is formed by one. Alternatively or in addition, the clamping means 7 can also be implemented hydraulically, pneumatically or by other spring or elastic elements. The clamping means 7 is intended preferably to effect clamping or holding of the pharmaceutical preparation/sample 2 between the electrodes 3.

In the illustrated example, the guide 6 forms a counter-bearing 8 for the clamping means 7. Alternatively or in addition the counter-bearing 8 can however also be implemented independently of the guide 6.

Preferably, the electrode 3A can be displaceable and/or moveable and/or slidable in particular axially in the measurement chamber 1 such that a space can be established between the electrodes 3 for insertion of the pharmaceutical preparation/sample 2. To do this, the guide 6 is preferably provided with a thread 9 which preferably engages an opposing thread 10. The opposing thread 10 is preferably connected to the measurement chamber 1 or is formed integrally with it. By turning the guide 6, it can be screwed farther into the measurement chamber 1 or out of the measurement chamber 1, as a result of which the space between the electrodes 3 can be adjusted. But, other approaches are also possible here for moving the counter-bearing 8 and with it the electrode 3A.

The electrode 3A can have a stop 11, an obstacle or a shoulder or the like which limits the mobility of the electrode 3A with reference to the measurement chamber 1 and/or the guide 6 and/or the counter-bearing 8.

One or more of the electrodes 3 has/have preferably a dynamometer 12 which is made and arranged to measure the force acting on the pharmaceutical preparation/sample 2. Preferably the dynamometer 12 is located between one of the electrodes 3 and the measurement chamber 1. But here other approaches are also possible. The dynamometer 12 can be used with a control loop and an actuator which is not shown to control a defined or definable force on the pharmaceutical preparation/sample 2, in particular by the clamping force of the clamping means 7 and/or the position of the counter-bearing 8 or the force acting on pharmaceutical preparation/sample 2 by the electrodes 3 being influenced.

In the illustrated example, in particular, the guide 6 can be rotated so that the force of the electrode 3A on the pharmaceutical preparation/sample 2 can be changed via the thread 9 and the clamping means 7.

The measurement chamber 1 preferably has a conditioning means 13 which is preferably made to influence, adjust or control the water content and/or the (relative) humidity of the atmosphere 4 by absorbing and/or releasing water.

The conditioning means 13 is preferably located in a holder 14 which is preferably located on one side of the measurement chamber 1 facing away from the electrodes 3. But, other approaches are also possible here. The measurement chamber 1 is preferably made in several parts and/or is formed multi-piece.

The measurement chamber 1 can be separated in particular into a part which has the electrodes 3 and a part which has the conditioning means 13 and/or the holding apparatus 14. To do this it is provided in the illustrated example that the parts of the measurement chamber 1 are sealed relative to one another in the closed state by a seal 15, the parts of the measurement chamber 1 being separable from one another along the seal 15.

Optionally, there can be a partition 16 or one can be inserted into the measurement chamber 1 in order to be able to operate the measurement chamber 1 with reduced closed volume in the region of the electrodes 3 without conditioning means 13. The side of the measurement chamber 1 with the conditioning means 13 can be removable in one version. In this case it is preferred that the partition 16 is or forms a cap, a closure or cover of the measurement chamber 1.

The electrodes 3 are preferably electrically connected to or by means of one or more cables 17 to a measurement apparatus 18. The cables 17 are preferably shielded and/or are anti-statically equipped to avoid disturbances of the measurement process.

Figure 2:
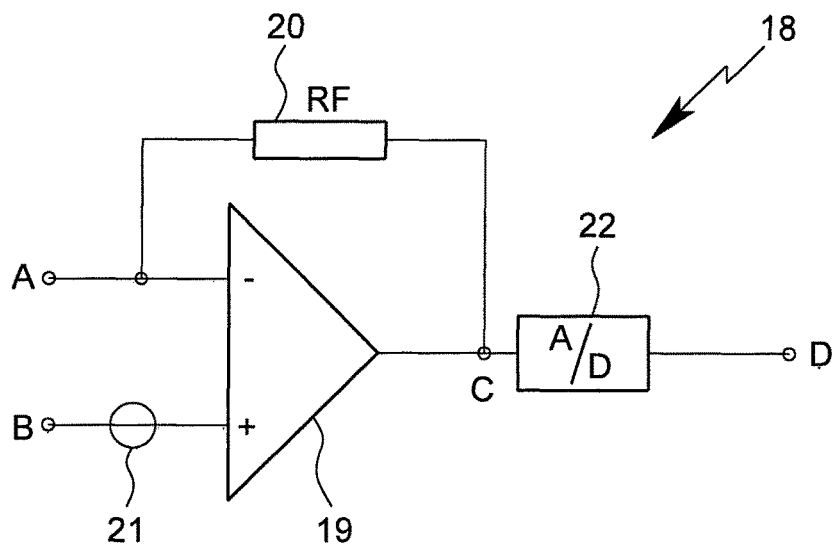
FIG. 2 is a circuit diagram of a proposed measurement apparatus.

FIG. 2 shows a schematic view of the measurement apparatus 18 in a preferred version. But alternatively, other approaches are also possible.

The measurement apparatus 18 in the example according to FIG. 2 has a negative feedback operational amplifier 19 as well as a feedback resistor 20. Between the nodes A and B which are connected to the inputs of the operational amplifier 19 and/or to one electrode 3 at a time, there is preferably the pharmaceutical preparation/sample 2, with which contact has been made by the electrodes 3.

The operational amplifier 19 in its interconnection according to FIG. 2 causes the differential voltage between the inputs identified with the plus sign and with the minus sign to become zero. It follows therefrom that the by a voltage source 21 in series circuit with the pharmaceutical preparation/sample 2, a voltage generated by the voltage source 21 drops on the pharmaceutical preparation/sample 2. Because the inputs of the operational amplifier 19 are high-resistance, the current produced by the voltage drop over the pharmaceutical preparation/sample 2 causes a voltage drop on the feedback resistor 20 which corresponds to the output signal of the operational amplifier 19 on the node C. The output signal is made available digitized preferably with an analog converter 22 at the output D of the measurement apparatus. For the principles in this regard reference is made here to the textbook *Halbleiter-Schaltungstechnik*, U. Tietze, Ch. Schenk, Springer Verlag, 11th Edition, 1999.

The voltage on the node C or the digitized signal corresponding or resulting therefrom on node D corresponds preferably to the resistance of the pharmaceutical preparation/sample 2. Here, it is assumed that due to the high resistance R of the pharmaceutical preparation/sample 2 parasitic effects by transition, supply leads or the like can be ignored. Alternatively or in addition, unwanted parasitic effects can be balanced by the measurement apparatus 18.

The analog output signal on the node C or the digital output signal on the node D of the measurement apparatus 18 is appropriate to the resistance R or corresponds to the resistance R, and within the scope of this invention for the sake of simplicity and clarity in the following is also designated "resistance R" or value of the pharmaceutical preparation/sample 2 corresponding thereto.

Figure 3:
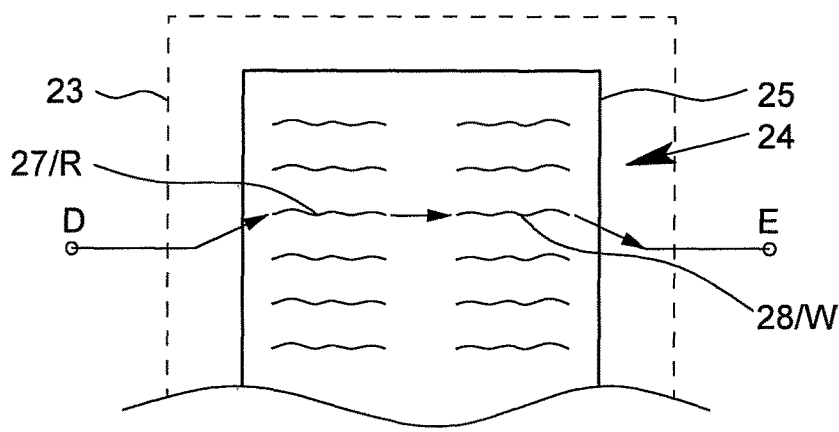
FIG. 3 schematically shows a proposed moisture determination apparatus.
Figure 4:
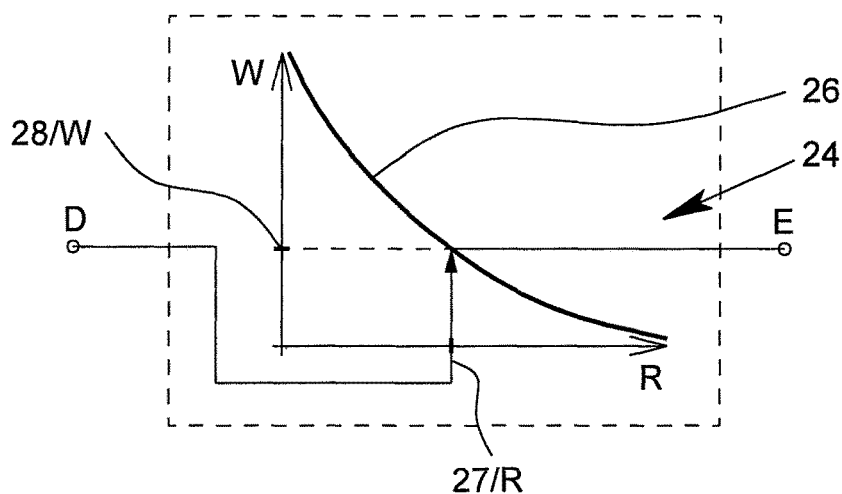
FIG. 4 shows an alternative moisture determination apparatus.

FIG. 3 shows, in a first version, a proposed moisture determination apparatus 23. The moisture determination apparatus 23 has preferably one assignment means 24, in the illustrated example an assignment table 25. Alternatively or in addition, it can also be an assignment function 26, as detailed in FIG. 4.

The moisture determination apparatus 23 is preferably made to determine with the assignment table 24 from the (ohmic) resistance R and/or from the value corresponding to it a corresponding water content W of the pharmaceutical preparation/sample 2. Here, a first value 27 which corresponds to or fits the (ohmic) resistance R can be used to read off or read out or calculate a second value 28 which corresponds to the resistance R or the first value 27 and which corresponds to the water content W of the pharmaceutical preparation/sample 2 and for the sake of simplicity and clarity is also called simply "water content" W. The water content W of the pharmaceutical preparation/sample 2 can be output at the output E of the moisture determination apparatus 23. In particular it can be displayed via a display 29.

In one preferred alternative, the water content W is transferred to a stability determination apparatus 30 which together with detailed information on one or more packaging systems calculates, forecasts and/or simulates the stability of the pharmaceutical preparation/sample 2 with the determined water content W of the pharmaceutical preparation/sample 2. In doing so, preferably, in addition water feeds and/or sorption and/or diffusion properties of the packaging material and/or of the pharmaceutical preparation/sample 2 are considered and/or combined.

As a result, on the node and/or output F of the stability determination apparatus a suitable packaging system, several suitable packaging systems, a stability of the pharmaceutical preparation/sample 2 in the state packed in one or different packaging systems, an additive demand, a desiccant demand, and/or several corresponding values or indicators or the like can be output and/or displayed with the display 29.

The assignment means 24 is preferably determined or can be determined by a calibration measurement. To do this, at least one pharmaceutical preparation/sample 2 is measured, therefore the resistance R of the latter is determined. Especially preferably using the measurement apparatus 18 several pharmaceutical preparations/samples 2 which have the same composition, but different water contents W are measured. Consequently, different ohmic resistances dependent on the respective water content W are determined by the measurement apparatus.

In the following, the actual water content W is determined below for the respective pharmaceutical preparation/sample 2 with a reference method. This actual water content W is assigned to the corresponding resistance R, as a result of which the assignment means 24 can be formed and/or constituted.

Pairs of values can be formed by the assignment of the respective actual water content W to the resistance R of the pharmaceutical preparation/sample 2 or values corresponding hereto. These pairs of values which correspond to an assignment of one respective resistance R to the water content W are preferably filed in an assignment table 25 and/or in particular are converted into an assignment function 26 by interpolation.

In the production of the assignment means 24 for the reference measurements and/or in later operation, preferably, the (respectively) identical ambient conditions, in particular with respect to the temperature and (relative) humidity of the atmosphere 4, are specified or set. In this way, the accuracy of the measurement method can be greatly improved.

Preferably, at least one, in particular several or all electrodes 3 in the measurement chamber 1 are interchangeable. In this way, the respective contact surface of the electrodes 3 can be matched or will be matched to the form of the current pharmaceutical preparation/sample 2. In FIGS. 5A to 5E, different schematic cross sections of potentially usable electrodes 3 are shown.

The electrodes are preferably at least essentially T-shaped and/or punch-shaped in cross section, but can also be made differently.

Figure 5A:
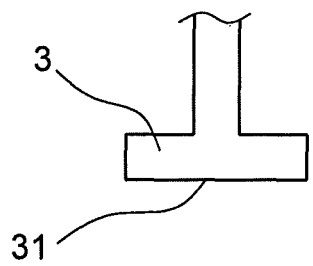
FIG. 5A to 5E show configurations of proposed electrodes.

The electrode 3 from FIG. 5A has at least one essentially flat and/or plane contact surface 31. The electrode from FIG. 5A is especially well suited for flat tablets or tablets with plane flat sides since flat contact can be produced; this improves the measurement accuracy and the probability of contact-induced errors is reduced.

Figure 5B:
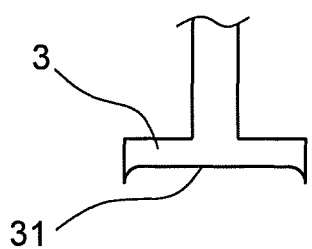

The electrode 3 from FIG. 5B has a preferably rotationally symmetrical contact surface 31 which is slightly arched concavely and/or to the inside and in which the radius to the axis of symmetry or the center axis increases. The contact surface 31 is made preferably complementary to tablets which are rounded on the edge and consequently fits them over a large area.

Figure 5C:
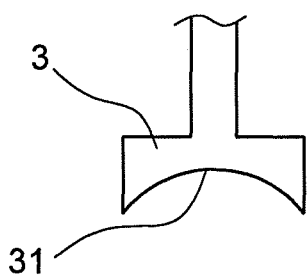

The electrode 3 from FIG. 5C has a contact surface 31 which is concavely curved with an essentially constant radius, in particular is continuously concavely curved, and which is advantageous in particular for making contact with lens-like or lens-shaped or also round tablets, since here too a comparatively large contact surface 31 between the electrode 3 and the pharmaceutical preparation/sample 2 can be achieved. The contact surface 31 can be rotationally symmetrical or oval in cross section.

Figure 5D:
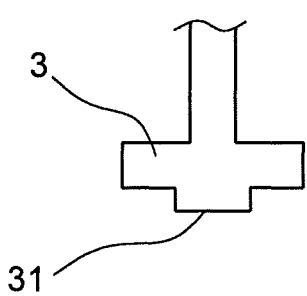
Figure 5E:
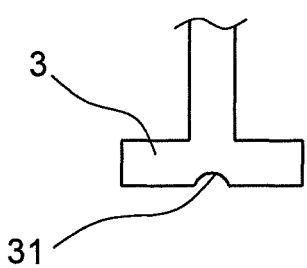

The electrode 3 from FIG. 5D has a punch-like contact surface 31 and/or a contact surface 31 with an area which is less than 0.5 times, preferably 0.25 times the diameter of the pharmaceutical preparation/sample 2 to be measured. The contact surface is made preferably at least essentially plane and/or flat. The electrode 3 offers the advantage of a defined contact surface even with unusual edge curvatures of the pharmaceutical preparation/sample 2. To achieve this, the contact surface can be or will be supported on the T-shaped base form.

The electrode 3 from Figure 5B has a preferably continuous and/or elongated receiver, arch or notch which can be formed in the manner of a hollow cylindrical section, preferably with a radius greater than 2 mm and/or less than 5 mm. In this way, contact with capsules can be optimally made.

In general the electrodes 3A, 3B are (each) made identical and/or have the same or similar contact surfaces 31. Something different can apply if asymmetrically formed pharmaceutical preparation/samples 2 are to be measured. Altogether, it is especially preferred that the contact surfaces 31 of the electrodes 3 are formed to be complementary to the presentation and/or the outer appearance of the respective pharmaceutical preparation/sample 2.

Figure 6:
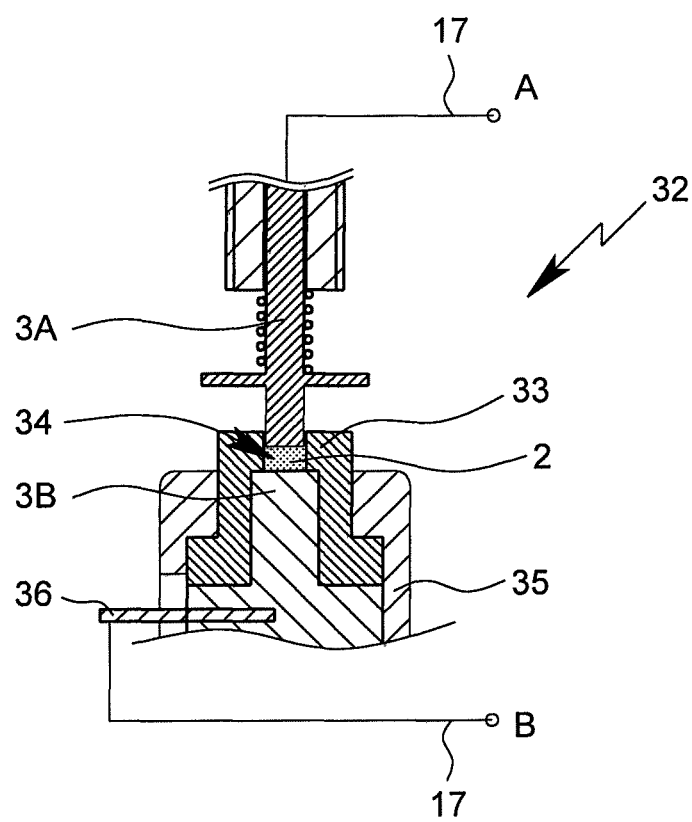
FIG. 6 is a cross-sectional view of a proposed electrode apparatus for measuring the resistance of a powdered or granular pharmaceutical preparation/sample.

FIG. 6 shows an electrode arrangement 32 in which, in addition to the electrodes 3A, 3B, there is a cavity 34 bordered by an insulator 33 for accommodating the pharmaceutical preparation/sample 2 in granular form or powder form.

Preferably, one of the electrodes 3A can move in the cavity 34 and/or is formed complementary thereto. In particular, one of the electrodes 3A with the cavity 34 forms, at least in sections, a cylinder-piston arrangement. This can result in that one of the electrodes 3A at least essentially covers the pharmaceutical preparation/sample 2 and/or makes contact with it over its entire area and/or compresses it, in particular by the tension of the clamping means 7.

A second or other of the electrodes 3B is located in the lower region in the electrode arrangement 32 from FIG. 6 and forms preferably at least in part the bottom of the cavity 34. In this way, large-area contact can be made and the resistance R, and consequently, the water content W can be accurately determined.

Optionally, the electrode arrangement 32 can also have an insulating cap 35, in particular a cap nut for fastening the insulator 33. Fastening can also take place differently.

Furthermore, the electrode arrangement 32 preferably has a contact pin 36 via which the cable 17 can be electrically connected to the electrode 3B. The upper electrode 3A can be pre-tensioned according to the design from FIG. 1 or some other way or have the clamping means 7. Alternatively or in addition to the clamping means 7, the electrode arrangement 32 can also have the dynamometer 12. But, here, other approaches are likewise possible.

The electrodes 3 of the electrode arrangement 32 can preferably be insertable into the measurement chamber or chambers 1 by replacement or insertion, and a measurement or evaluation can proceed accordingly as described in conjunction with FIGS. 1 and 2.

The measurement chamber 1 preferably has a chamber wall 37 which encloses, preferably airtight, the electrodes 3A, 3B and/or the electrode arrangement 32 and/or the atmosphere 4 and/or the conditioning means 13 and/or the holding apparatus 14. The chamber wall 37 can be formed from metal or other rigid materials. The chamber wall 37 preferably forms a hermetically sealable interior which is preferably filled with the atmosphere 4. The chamber wall 37 is preferably heat-conductive, cold-conductive and/or is made to supply energy to the atmosphere 4 and remove it from the atmosphere. The measurement chamber 1 can be located in a climatic test cabinet for adjusting the temperature or a climatic test cabinet can surround the chamber wall 37 to control the temperature of the atmosphere 4. The temperature of the atmosphere 4 is preferably controlled and/or regulated. This can take place from the outside by the chamber wall 37, but also by direct temperature control of the chamber wall 37 or of the atmosphere 4.

To ensure product quality of moisture-sensitive products packaging systems as tight as possible with the addition of generally granular desiccants are known.

A measurement of the preliminary moisture load with evaluated standard methods achieves at best an accuracy of +/−0.2% m/m, it is moreover time-consuming, fault-susceptible and destructive.

Figure 7:
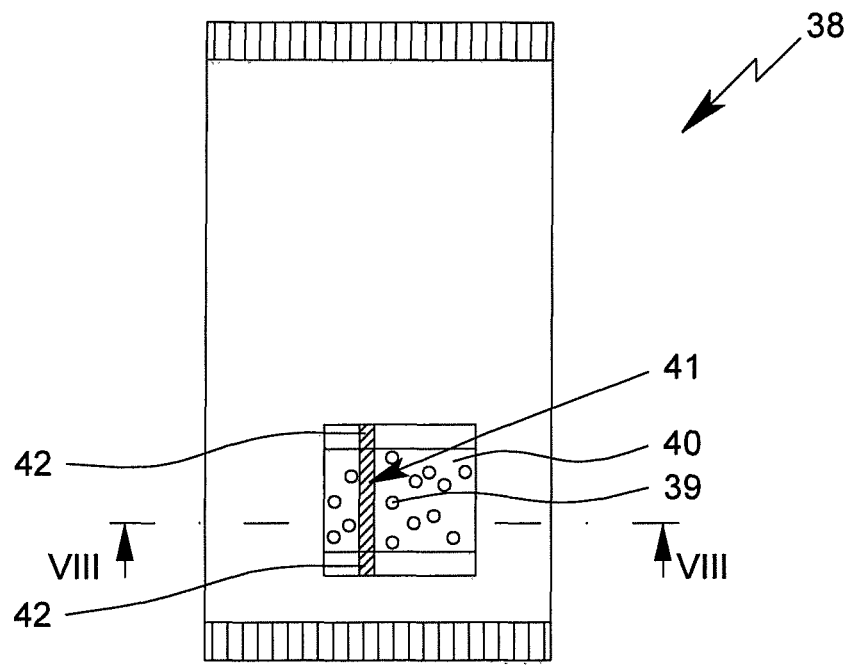
FIG. 7 illustrates a proposed packaging system.
Figure 8:
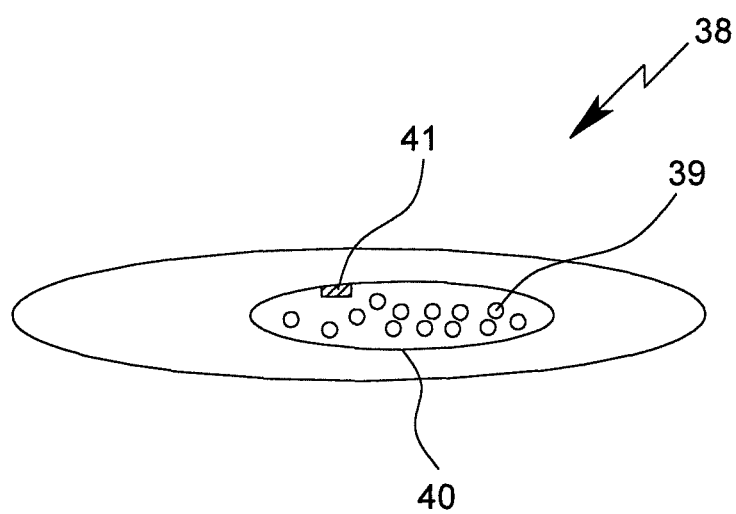
FIG. 8 is a section of the proposed packaging system taken along line VIII-VIII in FIG. 7.

One aspect of this invention which can also be implemented independently relates to a preferably bag-like package 40 (compare FIG. 7) for preferably granular substances and/or materials such as desiccants 39, the material which forms the package or a material placed in the package having a moisture-dependent resistance and forming a resistance apparatus 41.

The desiccants (typically silica gel, molecular sieve, bentonite or mixtures thereof) are generally used in packages 40 for desiccants, in particular sachets of HDPE fibers and/or PE fibers. These packages 40 are preferably at least partially permeable to water vapor in order to produce a separation between desiccant 39 and atmosphere 4, but at the same time to enable sorption of water by the desiccant 39.

Contact can be made with the resistance apparatus 41 preferably at different contact sites such that, between these contact sites 42, the resistance R of the resistance apparatus 41 can be measured. In the following, with the resistance R conclusions can be drawn about the moisture content/water content W of the resistance apparatus 41, and preferably, indirectly via this resistance R about the moisture content/water content W of the contents of the package 40, preferably of the desiccant 38.

The resistance apparatus 41 is preferably brought into thermodynamic equilibrium with the desiccant/the content of the package 40. In this way, via the resistance R of the resistance apparatus 41 the moisture content of the resistance apparatus 41 and indirectly the moisture content or loading of the desiccant/contents of the package 40 can be determined. To do this, assignment means 24 as described above can be produced and/or used.

It is preferred that the resistance apparatus 41 make contact with the moisture-dependent resistance R on different sides of the package 40 and the electrical conductivity and/or the resistance R is measured thereon.

Other steps, in particular calibration and measurement, can proceed as described above, preferably calibration taking place with the resistance apparatus 41.

Especially preferably, as the material with the moisture-dependent resistance or as the resistance apparatus 41, a resistance strip with moisture-dependent resistance R or a film with a moisture-dependent resistance R, preferably as an auxiliary strip, is placed in the package 40, in particular bonded in and/or shrink-wrapped. Preferably, the resistance apparatus 41 extends lengthwise along and/or within the package 40 between different, preferably opposite sides of the package 40.

Preferably, as resistance apparatus 41 a material which depending on the water saturation has a difference of resistance R in the configuration used by a factor of 10, 100 or 1000 is used.

Preferably oPA film (oPA=oriented polyamide) is used as a resistance apparatus 41, in particular in the form of an auxiliary strip.

This enables the use of the very strong moisture dependency of the electrical resistance of oPA film with a change by up to a factor 10000 in conventionally studied moisture ranges. With it, compared to conductivity measurement on conventional desiccant bags (for example, of GDT) an improvement by roughly a factor of 50 can be achieved. The method can also be used to measure the moisture content or water content W of other loose components and/or samples 2.

The use of an accompanying strip takes place especially preferably in the production of packages 40 from tubular continuous material, and the auxiliary strip can already be provided in the continuous material or can be introduced in the sealing and separation of bag-like segments, in particular can be bonded and/or shrink-wrapped on and/or in.

Furthermore, it is preferable to produce packages 40 in the form of sachet jackets for desiccants from a material with strong moisture dependency of the electrical resistance (for example, oPA). Alternatively or in addition this material can be woven into the fabric of sachet jackets in portions. This yields the advantage of being able to measure directly on the jacket material of the package 40; thus saves effort/costs of processing an auxiliary strip at the same time.

It is preferable to provide packages 40 of bulkware (for example, pouches, square bottom bags) with a resistance apparatus 41, in particular in the form of an auxiliary strip or the like, preferably on an inner side. This enables very accurate measurement of the relative humidity and thus the moisture content and water content W of the contents without opening and damaging the package. This offers the advantage of high accuracy of the moisture content measurement and a reduction of the risk of persistently damaging the package contents by the measurement process (opening and/or perforating).

It is suggested to, in general, provide packages 40, in particular desiccant containers (for example, bottle closures, desiccants and/or sorbent containing capsules) with a resistance apparatus 41, in particular in the form of an auxiliary strip, and in this way, also to enable moisture content measurements and/or water content measurements.

For example, Ca-based desiccant cards of fibrous material are being used. For improved measurement of their moisture content or water content W it is provided that they be cemented or bonded to a measurement apparatus 41 like to the auxiliary strip and/or to a film which can be used as described for measuring the moisture content of the card.

Furthermore applications are preferred in multilayer packages, for example, in so-called standard trough blisters. In one version the moisture/water content W in the package 40 can be measured via the conductivity and/or the resistance R of the trough film. The trough film is made or functions as a resistance apparatus 41 here.

According to one aspect of this invention the proposed method is also used for adsorbers for other volatile substances (for example, oxygen, odorous volatile substances, solvents). Their sorption capacity for volatile substances is generally also dependent on preloading with water. These absorbers (for example, iron oxide-, activated charcoal-, or zeolite-based sorbents) can likewise be used packed in sachets in granular form. Furthermore the method of moisture content measurement and/or water content measurement can also be used here for measurement of water preloading and thus its sorption capacity can be monitored and/or controllable for other volatile substances.

According to another aspect of this invention which can also be independently implemented, the electrical conductivity and/or the resistance R is also used for preliminary studies with respect to the sample quality of pharmaceutical active substances and/or ingredients and/or adjuvants.

One central idea of this invention is a quick, economical, nondestructive method which is improved in its accuracy and which can be used in a mobile manner to measure the moisture content in solid formulations of pharmaceutical products, their packages, packing means, components of packing means, in particular desiccants and films, packages and devices, in particular samples thereof, using the electrical conductivity and/or their electrical resistance R.

The electrical resistance R is defined as the reciprocal of the electrical conductivity, for which reason the terms can be used partially in correspondence or synonymously and/or are interchangeable.

The preferred measurement principle is based on the fact that the electrical conductivity of a sample 2 is dependent on moisture. According to one aspect of this invention which can also be independently implemented, it is differentiated between a resistance R and/or a conductivity or one or more resistances R and/or conductivities are taken into account which based on water ions themselves and a contribution of the ions mobilized by the water ions of the solid.

It is preferably assumed that there is a mathematically one-to-one and/or explicit, i.e. objective, relationship between the electrical conductivity and the moisture content. This relationship is preferably used as the assignment means 24 or for its determination.

The proposed method is based preferably on one or more direct current measurements (DC) of the electrical resistance R of the sample 2. Preferably the ohmic resistance R of the sample 2 is calculated from the measured voltage and measured or specified current.

The measurement unit and/or the measurement chamber 1 itself preferably has a precise electrometer. It is preferred that by means of the electrometer via the output of a constant high voltage and/or as a constant current source is used [sic].

The sample 2 is preferably high-resistance, for example, with more than 1 megaohm and/or a semiconductor. The sample 2 can also have a resistance R in the multi-digit megaohm range, for example, more than $10^8$, $10^9$ or $10^{10}$, in part up to $10^{13}$ or $10^{14}$ ohm towards $10^{15}$ ohm or even $10^{16}$ ohm. These resistances R are preferably measured to be able to draw conclusions about the moisture content and/or the water content W.

According to one aspect of this invention, the measurement chamber 1 between electrodes 3 insulated from one another and/or separated in space at least 5 mm has a resistance of more than $10^{16}$ ohm, preferably at least $10^{17}$ ohm. The measurement can be taken in an air-filled measurement chamber 1, at 25° C., normal pressure of 1013 hPa and/or a relative air humidity of a maximum 40%, preferably less than 30%, in particular less than 20% or 10%. Alternatively, the measurement is taken in technically dry, nitrogen-filled and/or evacuated measurement chambers 1. The measures taken to achieve this resistance, in particular highly insulated electrical feed lines and penetrations to the electrodes 3 advantageously enable a relatively accurate measurement of even very high sample resistances, as indicated above.

The high resistance values cause very small measurement currents (preferably less than 1000 pA, in particular less than 500 pA or 200 pA). For this reason it is preferred that creepage currents and capacitive effects on the apparatus be avoided or reduced, the latter mainly also on the samples 2. Vibration protection and/or an electrical or electromagnetic shielding in the measurement structure and/or specific sample holders for measurements on different forms of solid samples 2 are also advantageous.

The sample 2 is preferably used in a form in which it is or is to be packaged. In particular, it is a pharmaceutical preparation in the respective presentation, such as a tablet.

The sample 2 is preferably characterized as nondestructive, in particular, it is provided that the conductivity and/or the electrical resistance R of the sample is determined without the integrity of the sample 2 being adversely affected. The characterization of the resistance R or of the conductivity therefore takes place preferably nondestructively.

Preferably, calibration takes place. Preferably, the samples 2 are preconditioned for the calibration. In doing so the samples 2 can preferably be preconditioned with respect to the moisture content and/or water content W. To do this, preferably, both the moisture (water content W) and also the temperature of the sample 2 are preselected, for example, using a climatic test cabinet. Alternatively or in addition, the sample 2 can be stored in a tightly sealed vessel, for example, in a desiccator over a saturated salt solution at a certain relative humidity at a constant and defined temperature.

The sample 2 is preferably conditioned up to thermodynamic relaxation (complete matching to the temperature and in particular to the equilibrium moisture) for calibration. The relaxation times can be determined from DVS measurements, alternatively gravimetrically via relatively sensitive analysis weighings and/or by a highly sensitive measurement of the relative humidity for example, using micro-GC.

In operation relative to the actual determination, i.e., in the measurement of samples of unknown moisture, it should preferably be ensured that these samples are in a thermally relaxed state, i.e., in thermodynamic equilibrium both with their vicinity both with respect to the temperature and also with respect to the equilibrium moisture without the sample being reconditioned in doing so.

It is preferably assumed and/or care is taken that there has been thermodynamic equilibrium at sampling, i.e., that the sample has already been in climate control and briefly before removal within the material-specific relaxation time neither temperature nor relative humidity have changed. For transport to measurement and/or intermediate storage the temperature should only be changed to such an extent that phase transitions and all sorption-relevant effects are reliably precluded.

A change of the moisture content of the sample 2 before its characterization and/or before the measurement of its resistance R is prevented for example, by an at least essentially water vapor-tight package (Al pouches, stick packs, glass bottles with special closures—for example, with TEFLON®-based seals—and/or a relatively large amount of the sample and such a small surrounding gas space/atmosphere 4 that reconditioning by moisture exchange remains vanishingly small. The volume surrounding the sample 2 within such a package (atmosphere 4) is for example, less than 20%, 10%, preferably 5%, in particular 3% of the volume of the sample 2.

For the case in which it is unclear whether the sample 2 is in thermodynamic equilibrium and/or if a certain sample 2 regardless of its thermodynamic equilibrium is to be studied as quickly as possible using the electrical conductivity, the following possibilities are preferred.

In one version, the sample 2 is packed very tightly and with a small air space (small atmosphere volume) vapor diffusion-tightly and/or at a monitored and/or controlled temperature the relaxation times for the temperature equalization and moisture equalization are awaited at this temperature.

Alternatively or additionally, this process is accelerated by heating-up in the tight and relatively small package, preferably the relaxation time which is material-specific at the working temperature being awaited and the sample 2 then being cooled again to the measurement temperature.

In one especially preferred version, from the relaxing sample 2 at several different instants and/or at certain time intervals, for example, hourly, the resistance R and/or conductivity is measured (similarly to as in blood sugar or alcohol tests) and is extrapolated to the conductivity value or resistance R in the relaxed state.

So that conditioning is also ensured during the measurement, the measurement chamber 1 is preferably climate controlled and/or air-conditioned, for example, to 25° C. This is decisive for the measurement accuracy since with temperature the moisture content and/or water content W of the sample 2 could change (reason: temperature dependency of the sorption capacity) and/or the electrical resistance R changes (reason: thermal activation of the conductivity mechanism.

The conditioning can be implemented, for example, in a climatic test cabinet. Thus, as also in the calibration, the accuracy of the climatic test cabinet enters into the measurement. It has been ascertained in tests that the measurement accuracy with the proposed measurement chamber 1 is so high that the accuracy of the climatic test cabinet and that of the reference moisture measurement method (DVS) and optionally of the electrometer are the currently limiting factors for the accuracy of the moisture measurement methods described here.

For the accuracy and for the useful life of the apparatus during calibration and in measurement operation a stable moisture content and/or water content W of the sample 2 and thus a monitored and stable relative moisture in the sample chamber/atmosphere 4 is decisive.

Preferably all measurements take place in a sealed measurement chamber 1. The measurement chamber 1 preferably has a temperature-regulating apparatus such as a cooling apparatus like a compressor, a heating system such as a resistance heating system and/or a Peltier element, and preferably a temperature sensor with regulation for controlling the cooling apparatus and the heating system. In addition the measurement chamber 1 is preferably made for setting a certain (relative) humidity of the atmosphere 4 located in the measurement chamber 1.

Preferably, at least for the calibration, a constant climate is ensured with a saturated salt solution and/or preconditioned desiccant (for example, silica gel). The saturated salt solution and the preconditioned desiccant are located for this purpose preferably jointly within the measurement chamber 1 so that they are directly in contact with the atmosphere 4 within the measurement chamber 1. This combination links several advantages: it ensures the conditioning of the sample 2 also over a longer measurement time interval, the salt ensures a high sorption capacity (but is inert), the desiccant/silica gel conversely is very quickly in the moisture regulation of the chamber to the target value. This accelerates the measurement time by shortening the relaxation time after loading of the measurement chamber 1. The relaxation time can be checked with a injection/insertion probe The salt solution and the preconditioned desiccant can however also be used individually or can be located in the measurement chamber 1.

In measurement operation, a sample 2 of unknown equilibrium moisture can be studied without the stabilization of the measurement described above for calibration. To do this, for additional stabilization of the measurement (i.e., to ensure the original sample moisture and minimize the measurement error) beyond the sealing of the measurement chamber 1 the air space of the atmosphere 4 in direct contact with the sample can be reduced by a metal insert or other separation. This reduction of the amount of air and/or of the volume of the atmosphere 4 surrounding the sample 2 (which is enclosed jointly with the sample 2 inside the measurement chamber 1) minimizes the moisture turnover between the sample 2 and the air space/atmosphere. Alternatively, a smaller measurement chamber 1 can be used. Moreover, reconditioning of the sample 2 by the construction of the measurement chamber 1 and/or its parts can be minimized using materials with very low sorption capacities.

A further special challenge is the minimization of creepage currents outside the measurement chamber 1, for example, on the supply conductors, and within the measurement chamber 1. Preferably measurement lines and/or cables 17 are used which minimize creepage currents by highly insulating materials (in particular of the cable jackets). Furthermore, parts which come into contact with the sample in the measurement are preferably degreased. Moreover in particular vibrations in the supply conductors and/or cables 17 are inhibited, preferably secured against movement by a fastening. The supply conductors and/or cables 17 are preferably shielded against coupling of electrical, magnetic, and/or electromagnetic disturbances. Furthermore, the electrometer is preferably made to filter out or reject alternating signal portions.

Alternating signals are preferably signals which have frequency portions of several, preferably several hundred hertz or which consist thereof. Direct current or direct voltage is preferably also present when currents or voltages are slowly changed in a ramp-like manner or in some other way, for example, with a period of more than 100 ms, preferably 200 ms or 500 ms, in particular, a period of one or more seconds, preferably more than 2 or 5 seconds, in particular 8 to 15 seconds. It can also be sufficient if the direct current or the direct voltage is present over the duration of one such period.

The sample contacts/electrodes 3 can be formed from or can have a conductive material which is adaptable in form, for example, conductive rubber, metal brushes, metal wool and/or fibrous substances coated with a conductive material. To do this a soft, flexible and/or rubber-like punch, in particular silver-coated, which is adaptable in form and provided with a conductive layer, can be used. In another version, contacts of the electrodes 3 can be produced from the punch tools used in tabletting or similarly formed.

A further challenge in the measurements and evaluations are capacitive effects in the measurement apparatus. The samples themselves are generally semiconductors with very low conductivity. One of the consequences of this is that capacitive charging of the samples is inevitable. Simplified this means that of the total current which is flowing into a sample, one part is accumulated in the sample (capacitive portion) and another part flows out on the other side of the sample. Only this part of the current does in fact characterize the conductivity of the sample. In order to measure the conductivity itself as accurately as possible, preferably the van der Pauw method is used. It is based among others on special monitoring and/or controlling quickly of the potentials and a successive polarity reversal of the DC potential for eliminating the capacitive portions.

To optimize the measurements:
the number of polarity reversals to be carried out before the actual measurement can be determined, in particular for eliminating effects of static charging on the following measurement;
the relaxation times can be determined; and/or
the number of polarity reversals used for evaluation can be determined.

According to one further aspect of this invention, several samples 2 are conditioned to a certain moisture stage, to a certain identical moisture content or water content W. This takes place in particular for calibration, before calibration and or the calibration takes place with correspondingly preconditioned samples 2, of which consequently the certain moisture stage, the moisture or water content W is very accurately known or can be very accurately determined.

The preconditioning and/or the determination of the moisture stage, of the moisture or water content W takes place preferably with a so-called DVS balance or a DVS multi-sampler. Here, "DVS" preferably stands for the working principle of dynamic water vapor sorption.

Consequently, one of these samples is supplied to a sorption measurement and/or moisture content or water content determination and another of the samples to the proposed conductivity measurement.

According to one aspect of this invention which can also be independently implemented, the measurement chamber 1 has a DVS balance, there is a DVS balance in the or as the measurement chamber, the measurement chamber 1 forms a DVS balance or a part of it and/or the measurement chamber 1 works according to the principle of a DVS balance in particular for preconditioning.

A combination of the use of a DVS balance as a very accurate method for measuring the water sorption with a measurement of the relative humidity of the atmosphere 4 surrounding the sample 2 with the principle of so-called cavity ring down spectroscopy (CRDS) is furthermore preferred. Here, the actual moisture flow (relative humidity) which flows around the sample and/or the relative humidity of the atmosphere 4 flowing around the sample 2 can be routed through the CRDS apparatus. The CRDS apparatus can measure the moisture concentrations in a gas flow. In this way the accuracy in the relative humidity can be increased. Alternatively or in addition to CRDS, the oscillating crystal method for determining the relative humidity can be combined with the DVS method. The more accurate determination of the relative humidity makes it possible to further improve the limit of the accuracy of the proposed conductivity method.

In addition, reference is made to Richard A. Storey, Ingvar Ymen: *Solid State Characterization of Pharmaceuticals*, John Wiley & Sons Ltd, 2011 as well as G. Berden, R. Engelen: *Cavity Ring-Down Spectroscopy Techniques and Applications*, John Wiley and Sons, Inc. 2009.

Preferably, an assignment of stability-relevant parameters (for example, decomposition, dissolution, force at rupture (incl. brittleness and/or stickiness), appearance, physical-chemical phase instabilities) to the moisture content and/or the conductivity corresponding thereto or the resistance W of the sample 2 corresponding thereto takes place. This assignment is advantageous in particular:

a) In the setting of specifications: very accurately measured stability data (for example, of decomposition, dissolution, disintegration, etc.) can be assigned to much more accurately measured moisture content values/water contents W. The increased accuracy in the moisture content measurement thus increases the handling latitude for the packaging concept and thus for the marketing of the product (sample 2). This applies to all products with moisture specifications, but in particular to moisture-sensitive products.

b) In the checking of the moisture content, for example, in quality assurance, approval, ongoing stability, development, etc. This in turn increases the handling latitude for the packaging concept and marketing.

c) In the checking/release of the bulkware (sample 2) for packaging. This increases the safety of the product (packaged sample 2), leads to a reduction of bulkware to be used (sample 2) and thus saves resources and costs.

d) In especially complex cases it can happen that handling latitude for certain packaging concepts is only provided by an increase of the accuracy of the moisture content measurement methods. This applies in particular to especially moisture-sensitive products and/or to marketing in climatic zones with increased moisture and temperature and/or depending on the medication pattern, with very challenging in-use conditions. In such complex configurations it can also happen that according to the current state of the art bottles with a maximum amount of for example, 7.8 g of desiccant could not prevent the maximum allowable moisture content from being exceeded.

The proposed measurement method for the moisture content enables optimization of the demands on the tightness of the packing means, of packaging concepts, as well as optimization of desiccant amounts, enables more exact knowledge of safety margins in the packaging concept and being economical with it in QS (for example, definition of maximum preloading with moisture and/or minimum residual sorption capacity of desiccants) and in the process chain (for example, maximum machine standstill times, in particular in which the sample 2 is exposed for a time longer than usual in an unscheduled manner to an environment from which the sample 2 can absorb water). Thus, the over-dimensioning of packaging concepts and safety margins practiced to date among others for compensation of measurement accuracies are reduced in processes. This leads to safer products, and at the same time, fixed-cost packaging concepts as well as processes.

The measurement time for the conductivity is preferably a few minutes per sample 2. Together with the accuracy an advantage arises compared to standard methods and even compared to the laboratory reference method of DVS sorption measurement which was considered to date the "gold standard" in its accuracy. There the moisture content measurement lasts between 30 minutes and several months, depending on the product/sample 2.

Advantageously, the measurement is nondestructive. The same sample 2 can be supplied to further study methods (for example, decomposition, dissolution, breaking force, structure studies, IR, Raman, microscopy, NMR, CT and/or study of phase transitions). Combination of results in many cases yields improved meaningfulness, in particular by a much more accurate assignment of stability-relevant parameters and moisture content. For especially expensive products the sample 2 can even be supplied again to the original use.

In contrast to the reference method (DVS), comparable solely with respect to its accuracy, the conductivity method can be used in a mobile manner. This enables its use in QS during the process chain.

The particular combination of promptness and/or quickness, nondestructiveness and mobility of the conductivity measurement in bulkware production, random sample studies, in their storage, release to production, but in particular in machine standstill, and/or in intermediate storage of the product, for example, prior to delivery, or however of blisters before placing in pouches. Other possible applications arise as measurement methods for differences, for example, reliable characterization of bulkware in damaged large bunches. Its accuracy, promptness and/or quickness, nondestructiveness and mobility make the method usable at-line, on-line and in many cases even in-line. The enables a significant quality and efficiency increase and cost reduction.

The proposed method does not require any preparation and/or intervention on the sample 2 itself. This enables the development of a very user-friendly measurement apparatus according to the "gate open—sample 2 clean—gate closed—measure" concept. The exposed storage time of the sample 2 which is thus drastically reduced associated with the simple handling is a decisive advantage compared to established methods towards much lower fault susceptibility and still higher accuracy than in previous test measurements.

The proposed method does not require any heat burdening of the sample; in this way, a reduction of potential fault sources and reusability of the sample for comparison measurements is enabled.

The proposed method does not require consumable materials; compared to other methods this leads to cost minimization incl. elimination of disposal costs for environmentally toxic wastes.

In another exemplary embodiment, the method is also applied to multi-component systems, for example, for multilayer tablets. To do this, for example, the surface resistance can be measured as desired on the most quickly sorbing component and/or on the most moisture sensitive component and/or the component with the strongest signal. Conclusions about the moisture content and/or water content W of the components which have not been measured can be drawn from the knowledge of the sorption capacities and kinetics of the individual components.

Alternatively or in addition, on one or more components/samples 2 both the surface resistance as well as the volume resistance are measured. Conclusions about the moisture content/water content W of the overall system are drawn from the comparison of the two measurements.

In accordance with a further aspect, moisture content measurements are taken on tablet coatings. With the measurements especially on coatings, the effort for the proposed method can be reduced. The fact that moisture content measurements can also be taken on coatings themselves enables measurement of sample moisture by measuring the surface resistance in the coating layer separately from the remaining sample. For a sample 2 in thermal equilibrium the surface measurement at the same time reflects the property, i.e. the moisture content of the entire sample 2.

This invention preferably enables "platform solutions" with availability of a simplified apparatus for all products (samples 2) with a certain coating. The consequences are for example, fewer measurement ranges, less adjustment effort, a simplified measurement method, optimization of the currents and output voltages to the most suitable measurement range, simpler method development, reduction of error sources in operation, more safety and thus a cost reduction.

This invention preferably enables the use of coatings as "applied sensors": coatings with an especially high moisture dependency of the electrical resistance R could be selected in a controlled manner and/or specifically selected and used as "applied sensors" and/or resistance apparatus 41 for measurement. It can be assumed that by means of the resistance R conclusions can be drawn about the moisture content and/or the water content W of the entire sample, in particular if a thermodynamic equilibrium and/or equilibrium moisture between the coating and remaining sample 2 is assumed.

This is advantageous mainly in tablets which themselves have a low moisture dependency of the conductivity and/or the resistance R. This expands the use of the method with all the resulting advantages.

According to one aspect of this invention, with the proposed method, the moisture/water content of a capsule and of capsule contents is determined separately from one another, preferably with the proposed method or the proposed measurement chamber 1. Since capsule materials compared to formulations can partially take up considerable amounts of water, the water content of capsule materials plays a special part. A measurement of this quantity as accurate as possible is especially helpful prior to the time of packaging. The proposed method can be applied in particular to HPMC, hard and soft gelatin capsules, and polymer-based capsule materials.

The electrical conductivity in a bulk material is among others given by the number of current paths and by the individual contact resistances between the particles through which the current flows in series and/or in parallel. Therefore especially in bulk materials at least statistical monitoring and/or controlling of the contact surfaces, for example, via the material density, is helpful for meaningful and reproducible results. Advantages are achieved here in that the samples 2 are exposed to a defined pressure. To do this loose samples (for example, pellets, granulate, powder, compactate) are placed in a mount of highly insulating plastic for measuring conductivity and compacted with a punch at a defined pressure. In order to prevent change in the material, a pressure below the (or a typical) tableting pressure is chosen. A compacted sample is formed which has a much better defined density than the pertinent loose material. In this way conductivity measurements with a very good signal to noise ratio and/or low uncertainty factor and good reproducibility can be taken. Preferably for simplification or for optimization of the measurement (optimum contact area) the pressure punch is used as an electrical contact.

In another preferred embodiment, first the pressure dependency of the electrical resistance R is determined at constant moisture content/water content W of the sample 2. This follows the underlying idea that often a so-called "pressure plateau" can be found in which the electrical resistance R remains (almost) constant over a certain pressure range or changes less than in other segments, therefore current paths and contact surfaces do not change significantly. The later measurement of the moisture dependency of the electrical resistance R then takes place at a constant pressure value on the pressure plateau, preferably at a pressure value in the middle of the plateau. This reduces disturbances and thus error sources by the pressure dependency of the electrical conductivity. Elimination of the pressure dependency of the electrical conductivity as an error source also yields advantages with respect to improving the meaningfulness of the measurement, i.e. the one to one assignment of the resistance R to the moisture content/water content W and improvement of the accuracy of the measurement.

One aspect of this invention which can also be independently implemented relates to the determination of the moisture or of the water content of packaging materials, in particular packing means such as films and/or desiccants, the latter in particular in order to determine the preloading of the desiccant with moisture.

Especially in packing means, in particular in polymer-based ones, can the electrical field line characteristic in the sample 2 and electrostatic stray fields influence the measurements? Preferably therefore, in particular in packing means, using a point-symmetrical Corbino geometry can a measurement be taken. In this way, a very homogeneous electrical field is implemented in the sample and at the same time the effect of stray fields is minimized. The Corbino geometry can however also be used on other samples.

Corbino geometry is preferably a disk-shape, preferably at least essentially round, flat or plate-shaped and/or film-like sample. The electrical current runs from a center electrode in the center of the disk or at the center of gravity to a preferably annular or peripheral outer electrode and/or one which is located on one outer edge.

Preferably, there is a magnet and/or a coil located concentrically to the disk. An in particular at least essentially homogeneous magnetic field runs perpendicular thereto. If either the magnetic field or the current through the disk is started or stopped or changed, as a result of the Hall effect one current at a time is induced in the coil. In one preferred version however only the disk arrangement without the magnetic field and coil is used. Easily reproducible results have also been shown in the above described procedure of resistance measurement.

In another embodiment, the surface resistance can be measured instead of the volumetric resistance. This can be especially advantageous for exposed samples (films, devices, components, in particular desiccant cards). In particular from the comparison of surface resistance and volumetric resistance both the surface contamination and also overall loading of the sample with moisture can be determined. This is advantageous in exposed storage of packing means for example, in a production process, in particular in machine standstill.

According to another aspect of this invention, surface measurements and volume measurements of the electrical conductivity are determined and preferably compared to one another. From the comparison of the measurements a depth-moisture loading profile of the sample 2 during moisture exposure can be prepared. Moisture content measurement in thermodynamic disequilibrium makes it easier to improve the quality assurance and cost efficiency by reducing scrap.

Preferably, the method is used for cover films in particular for moisture content measurements on highly water-sorbing hot sealing lacquer (HSL). This can take place as a surface or volume measurement or in combination of the two. Monitoring and/or controlling of the moisture loading by the HSL is important in particular in inhalants. This is advantageous in exposed storage of packing means for example, in a production process, in particular in machine standstill.

In another variation, in particular in exposed composite films, that layer is measured which shows the higher signal/noise ratio. With the sorption curves and the respective take-up kinetics for water, conclusions can be drawn about any other components under the same climatic conditions (for example, packing means, device). This is advantageous in exposed storage of packing means for example, in a production process, in particular in machine standstill.

To ensure the product quality cards of moisture sensitive products, sorbents (for example, desiccants) also in the form of polymer-based cards or moldings doped with ground desiccant can be added to the package.

Desiccants and/or desiccant cards based on PP or PE, doped with a molecular sieve (MS), silica gel (SG) and/or bentonite can be provided, preferably each in weight portions between 35% and 60% m/m. Components of a secondary and/or primary package (for example, the cap of a commercially available pregnancy test) can be doped with a sorbent, alternatively or in addition device components (for example, the housing of an inhaler or moldings for protecting a blister).

It is preferable to determine the water content of desiccant cards (TMK) likewise using the electrical conductivity, for example, on TMK of PP doped with MS. In an attempt to conventionally determine the moisture preloading or the current residual sorption capacity of these moldings, in particular TMK, for purposes of quality assurance, basic physical limits are encountered. Heating-up is not meaningful since there is the risk of heating up more than only water and/or destroying the material. Gravimetric determinations fail in practice because sorption experiments on these TMK would last several weeks. Moreover they would enable only a very inaccurate indication of the preloading with water.

In the components discussed above, those with maximum doping play the most important role since package size and costs are minimized therewith. Still, for example, for reasons of mechanical properties, the size of a device or functional molding it can be necessary to dope such a component with smaller amounts as sorbents. The possibly lower sensitivity of the measurement method on the components themselves can be compensated by for example, a film with very high moisture sensitivity of the electrical resistance (for example, oPA) being processed at the same time (for example, as an auxiliary strip, cover film or as a solidly processed part of the device components or packages). Alternatively or in addition the carrier material of the components can be produced from this material (for example, oPA).

It is preferable to work an auxiliary strip of a plastic doped with a molecular sieve into the bag. The water content of the molecular sieve contained in it very accurately reflects the water content of the granular molecular sieve.

In very special cases multifunctional desiccant mixtures (for example, of MS and SG) are used. This approach can also be used for these mixtures: To do this it is proposed that the sensor unit (doped auxiliary strip, TMK, device components, etc.) be composed of one doped with MS and in parallel one doped with SG. This enables wide-scale measurement over the entire moisture range.

The proposed measurement principle can be used on desiccant cards based on Ca. An application in desiccant-containing films and/or in flexible desiccant film inserts which are adapted to the interior of a package (for example, of a bottle) is likewise possible.

In many cases the components to be measured can be relatively thick so that in moisture exposure in the material (sample 2) a moisture gradient can form within the material. In these cases both the surface resistance and also the volumetric resistance of the sample 2 can be measured. This makes it possible to determine the surface and volumetric contamination and to accurately measure the moisture content and/or the moisture characteristic/the moisture distribution within the sample 2 in these cases as well.

In addition to pharmaceutical products and devices for their use, the invention can also be used, for example, in diagnosis systems or plastic cards with reagent-containing components, so-called diagnosis cards. These and other apparatus should be stored and/or used in a certain moisture corridor, that means neither certain low relative humidities should be undershot nor certain higher relative humidity values should be exceeded.

To ensure the stability and/or functionality of such a card (sample 2) the moisture in the packaging unit, preferably on the card itself or in its package, can be measured using the conductivity method directly before release for delivery or directly for use.

To do this, the package can have an auxiliary strip (for example, oPA) as an integrated moisture sensor and/or resistance apparatus 41. Furthermore the use of a film (for example, oPA) suitable for resistance measurement as a sealing film on the card or on parts thereof, or as a paste for implementation of the resistance apparatus 41 is possible. Alternatively or in addition, the preparation of the diagnosis card itself from a plastic is suitable for measurement of the moisture content via the conductivity is preferred. In one version the card material is doped with desiccant and optionally preconditioned wet. The moisture content of the system is preferably measured by resistance measurement on the card itself or on its package.

Another possibility is the use of the chip of an integrated diagnosis circuit for measuring the moisture content via its resistance. The integration of a conductivity moisture sensor into the chip and/or on the chip (for example, application of a film, for example, OPA, between two pins) is alternative or additional. In this way the equilibrium moisture and thus the water content of the individual components of the entire system can be determined.

In another aspect of this invention, the method of electrical conductivity is used to monitor and/or control and/or determine the hardness, brittleness and/or stickiness of tablets and/or capsule (for example, polymer-based capsule and/or gelatin capsules).

Measurements for monitoring and/or controlling the hardness, brittleness and stickiness of tablets or capsules are relatively expensive and mainly in elastically and plastically deformable samples are often ambiguous and/or burdened with artefacts. Moreover they are relatively time-consuming. In the past efforts have often been made to monitor and/or to control these stability-critical parameters via the moisture content. With this invention it is possible for better monitoring and/or controlling to measure stability-critical parameters using moisture-preconditioned samples 2 and to identify a critical value and/or range of certain relative humidities (of the atmosphere 4 and/or the sample 2). On equally conditioned comparison samples the electrical conductivity (resistance R) is measured as a function of the relative humidity of the atmosphere 4 surrounding them. Then the conductivity and/or the resistance R with its respective stability-critical parameters is identified on a one-to-one basis. Thus the conductivity can be used to indirectly monitor and/or to indirectly control these parameters.

Measurements for monitoring and/or for controlling the dissolution or disintegration are relatively time-consuming and can be taken mainly within a production process only with a certain delay. To date efforts have often been made to monitor and/or to control these stability-critical parameters via the moisture content/water content W. In this context the proposed method can also be used in the determination of the electrical conductivity.

Measurements for monitoring and/or controlling the proportion of fine particles of inhalation powders are especially time-consuming and can be taken mainly within a production process only with a certain delay. To date efforts have often been made to monitor and/or to control these stability-critical parameters via the moisture content or water content W. In this context the proposed method can also be used in the determination of the electrical conductivity and/or of the resistance R.

Measurements for monitoring and/or for controlling the sample quality or of the ageing state of samples 2 are especially expensive. In particular, it is very complex to recognize the instant or the external parameters under which the sample quality could change without for this purpose carrying out a complete study with the standard methods available for this purpose. This applies among the solid forms to the samples 2, such as for example, adjuvants, active substances and/or ingredients, intermediate products, freshly produced tablets, capsules, as well as after tabletting, for example, tablets or capsules aged or relaxed with equalization of local stresses. In order to be able to improve monitoring possibilities in this respect, with this invention very sensitively possible changes in the sample quality can be recognized early and the samples 2 can be supplied to more accurate studies with respect to the stability-critical parameters. The strength of the method is its very high sensitivity relative to ion concentrations, for example, by the presence of impurities, fluctuations in the proportions of a mixture and in the ion mobility, for example, different and/or changing conformations, crystallinity or interactions of different components of a mixture.

It is possible to assign higher ion mobility to possible higher reactivity, optionally with stability-relevant aspects, and/or lower ion mobility to higher interactions, optionally with stability-relevant aspects, for example, for breaking force, disintegration, dissolution.

In samples/formulations which show changes in the calibration of the conductivity curve, this calibration is carried out preferably on reset samples directly before the measurement campaign. The measurements themselves last a few minutes per measurement point.

So far the measurement principle has been described as a direct current measurement (DC) with stepped polarity reversal of the current direction with a very low frequency. Depending on the material-specific capacitive portions of the charge distribution in the samples 2 and in the apparatus and/or the measurement chamber 1, in one version an alternating current measurement (AC) can be used alternatively or in addition. In this way the type of charge carriers contributing to conductivity and/or their mobility (for example, electron and/or ion conduction, interactions, for example, water of crystallization) can be determined.

The measurement principle is preferably carried out at a constant temperature, preferably near room temperature, for example, at 25° C. However it is possible in other versions alternatively or in addition to pass over to measurements at other temperatures, for example, more than 30° C., in particular more than 40° C. and/or less than 80° C., preferably less than 70° C. or 60° C.

In multicomponent systems and/or samples, both electrons and also various types of ions can contribute to conductivity. In particular, against this background of diversely possible interactions and their complex temperature dependency, the temperature dependency of the electrical conductivity can be difficult to predict. Still, an increase of the measurement temperature could cause a high signal difference in the moisture dependency of the conductivity. This was done intentionally by way of example on a substance with a signal difference which was rather small at 25° C.

In other versions, measurements in thermodynamic disequilibrium to study the reconditioning of a sample are possible. A thermodynamic disequilibrium immediately starts moisture reconditioning of the sample and during the material-specific relaxation time within the sample optionally a gradient in the moisture content occurs. Such a sample can be viewed in an equivalent network as a chain of resistances connected in series and in parallel. A one-to-one relationship between resistance and moisture content is first of all no longer present since in a thought experiment a relaxed sample (without internal moisture gradient) and an unrelaxed one (with internal moisture gradient) could theoretically show the same resistance, but could have different moisture content.

Preferably, in particular, when it is necessary to measure in thermal disequilibrium, for example, to reproduce the effect in exposed storage during certain process steps, a sufficient sample amount is conditioned up to thermal relaxation to the water content which is relevant there (for example, bulkware specification). Then, a sample 2 is supplied to conductivity measurement/proposed resistance measurement and another part of the sample amount to precise weighing and/or reference measurement.

Subsequently, the differing climate and/or the differing relative humidity of the atmosphere 4 surrounding the sample is produced in order for example, to simulate exposed storage. In doing so, preferably at the same time both the resistance on one sample and also the moisture content on the other sample quantity are gravimetrically measured. Thus, there is a clear correlation between the thermal disequilibrium by the differing climate on the resistance and the influence on the moisture content. With this relationship, conclusions can preferably be drawn about the water content or the moisture.

Preferably, the change of the moisture content over time on a completely exposed sample is measured. Thus, there is a one-to-one relationship between a resistance value R and the pertinent moisture content value in this climate at any time. Consequently, the effect of the contact arrangement or of the electrodes 3 can be negligible.

The procedure is especially advantageous in threatening reconditioning of samples 2, in particular in machine standstills, since the surface reacts especially quickly to changes of the moisture content.

This invention can generally be used to measure the moisture content of solids and/or solid samples 2 and/or samples 2 of solid materials, in particular pharmaceutical preparations and/or packaging materials.

Different aspects of this invention can be implemented and can be advantageously individually and in different combinations.

What is claimed is:

1. A method for determining water content of a sample, comprising:
    bringing at least two electrodes into direct contact with the sample in a measurement chamber such that the electrodes are electrically connected to one another via the sample,
    determining a resistance of the sample by means of the electrodes, and
    determining the water content of the sample using the resistance determined,
    setting or specifying the water content or relative humidity of a temperature controlled atmosphere in the measurement chamber surrounding the sample during a measurement,
    wherein the sample is at least one of a powder pharmaceutical preparation, or a solid pharmaceutical preparation, and
    wherein the sample inside the measurement chamber is brought into direct contact with the electrodes with a pressure force being exerted by the electrodes on the sample that is predetermined.

2. The method as claimed in claim 1, wherein an assignment means is used to determine the water content, the assignment means assigning a water content of the sample which has been determined with a reference measurement method to resistances determined at the same water content of the sample, respectively.

3. The method as claimed in claim 2, wherein for each combination of a certain presentation of the sample and certain electrodes, an individual assignment means is determined or used.

4. The method as claimed in claim 2, wherein a water content which corresponds to the resistance is determined by the assignment means, and the water content or a stability or a quality of the sample which has been determined therefrom is output as a result.

5. The method as claimed in claim 1, wherein for a certain configuration of the sample, corresponding shaped electrodes are mounted in the measurement chamber, exchanged or connected to a measurement apparatus for measuring the resistance of the sample.

6. The method as claimed in claim 1, wherein the setting or specifying of the water content or relative humidity of an atmosphere surrounding the sample in the measurement chamber is performed using a conditioning means provided in the measurement chamber.

7. The method as claimed in claim 1, wherein the same composition and/or temperature of the atmosphere is used inside the measurement chamber as is used in packaging of the sample.

8. The method as claimed in claim 1, wherein an ohmic resistance of the sample is used for determining the water content of the sample and/or for prediction of the stability of the sample in a particular packaged form.

9. A measurement chamber for determining a resistance of a sample, comprising:
    a housing,
    at least two electrodes disposed within the housing the electrodes being configured to accommodate the sample between them and to bring the sample into direct contact with the electrodes for electrically connecting the electrodes to one another by the sample so that the resistance of the sample can be determined via the electrodes,
    wherein the housing is sealable airtight and encloses a temperature controlled atmosphere which surrounds the sample, the sample being at least one of a pharmaceutical preparation or a packaging material,
    wherein the housing is set up to adjust a water content or a humidity of the atmosphere enclosed by the housing,
    wherein the electrodes are movably held relative to one another in the measurement chamber, and
    wherein a clamping means is provided for pressing the electrodes against the sample with a force exerted by the electrodes on the sample that is predetermined.

10. The measurement chamber as claimed in claim 9, wherein the pharmaceutical preparation is one of a solid pharmaceutical preparation or a powder pharmaceutical preparation.

11. The measurement chamber as claimed in claim 9, wherein the electrodes have contact surfaces that have a shape that is at least essentially complementarily to a surface of the sample.

12. The measurement chamber as claimed in claim 9, wherein the electrodes are interchangeable with others of a set of electrodes so that electrodes that either correspond to a form or configuration of the sample or which are made of a material which is adaptable to the shape of the sample surface are selectable.

13. The measurement chamber as claimed in claim 9, wherein the measurement chamber has a measurement apparatus which is configured to measure the resistance and which is electrically connected to the electrodes.

14. The measurement chamber as claimed in claim 9, wherein the measurement chamber has a moisture determination apparatus for determination of the water content which corresponds to the resistance.

15. The measurement chamber as claimed in claim 9, wherein the measurement chamber has a stability determination apparatus which is configured to calculate a stability of the sample when stored inside a certain package using the water content.

16. A method for determining water content of a sample, comprising:

bringing at least two electrodes into direct contact with the sample in a measurement chamber with a predetermined pressure force of the electrodes on the sample in a manner causing the electrodes to be electrically connected to one another via the sample, determining a resistance of the sample by means of the electrodes, and determining the water content of the sample using the resistance determined, and setting or specifying the water content or relative humidity of a temperature controlled atmosphere in the measurement chamber surrounding the sample during a measurement, wherein the sample is a packaging material.

17. A measurement chamber for determining a resistance of a sample, comprising:

a housing, at least two electrodes disposed within the housing the electrodes being configured to accommodate the sample between them and to bring the sample into direct contact with the electrodes for electrically connecting the electrodes to one another by the sample so that the resistance of the sample can be determined via the electrodes, wherein the electrodes are movably held relative to one another in the housing, wherein a tensioning means is provided for pressing the electrodes against the sample with a reproducible defined force, wherein the housing is sealable airtight and encloses a temperature controlled atmosphere which surrounds the sample, the sample being a packaging material, and wherein the housing is set up to adjust a water content or a humidity of the atmosphere enclosed by the housing.

18. The measurement chamber as claimed in claim 17, wherein the electrodes have contact surfaces that have a shape that is at least essentially complementarily to a surface of the sample.

* * * * *